United States Patent
Chu

(10) Patent No.: US 6,451,768 B1
(45) Date of Patent: Sep. 17, 2002

(54) MACROLIDE ANTIINFECTIVE AGENTS

(75) Inventor: Daniel T. W. Chu, Santa Clara, CA (US)

(73) Assignee: Kosan Biosciences, Inc., Hayward, CA (US)

( * ) Notice: Subject to any disclaimer, the term of this patent is extended or adjusted under 35 U.S.C. 154(b) by 0 days.

(21) Appl. No.: 09/551,162

(22) Filed: Apr. 14, 2000

Related U.S. Application Data

(63) Continuation of application No. 09/550,045, filed on Apr. 14, 2000.
(60) Provisional application No. 60/173,805, filed on Dec. 30, 1999, provisional application No. 60/173,804, filed on Dec. 30, 1999, provisional application No. 60/172,159, filed on Dec. 17, 1999, provisional application No. 60/172,154, filed on Dec. 17, 1999, provisional application No. 60/140,175, filed on Jun. 18, 1999, and provisional application No. 60/129,729, filed on Apr. 16, 1999.

(51) Int. Cl.[7] ............ A61K 31/70; C07M 17/08
(52) U.S. Cl. ............ 514/29; 536/7.2; 536/7.4
(58) Field of Search ............ 536/7.2, 7.4; 514/29

(56) References Cited

U.S. PATENT DOCUMENTS 5,141,926 A  8/1992  Weber et al. ............ 514/29

(List continued on next page.)

FOREIGN PATENT DOCUMENTS

FR  2754821  4/1998

(List continued on next page.)

OTHER PUBLICATIONS

Weber J.M. et al. (1991). *Science* 252:114–117.

*Primary Examiner*—Elli Peselev
(74) *Attorney, Agent, or Firm*—Kevin Kaster; Carolyn A. Favorito

(57) ABSTRACT

Compounds of the formula

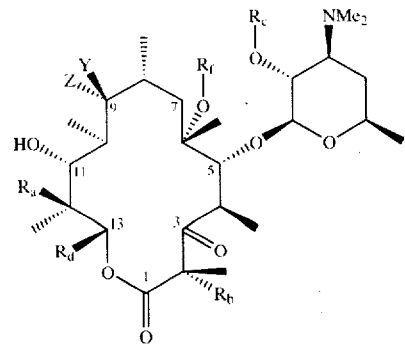

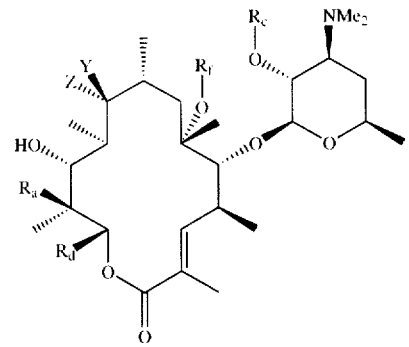

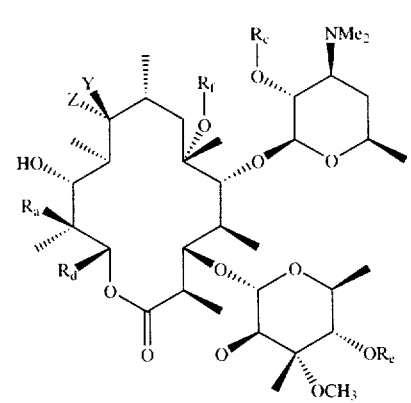

or the 10,11-anhydro forms thereof wherein
$R_a$ is F or OH;
$R_b$ is H or halogen;
$R_c$ is H or a protecting group;
$R_d$ is methyl; unsubstituted alkyl (3–10C); substituted alkyl (1–10C); substituted or unsubstituted alkenyl (2–10C) or substituted or unsubstituted alkynyl (2–10C); substituted or unsubstituted aryl (4–14C); substituted or unsubstituted arylalkyl (5–20C); substituted or unsubstituted arylalkenyl (5–20C); substituted or unsubstituted arylalkynyl (5–20C); substituted or unsubstituted amidoarylalkyl (5–20C); substituted or unsubstituted amidoarylalkenyl (5–20C); or substituted or unsubstituted amidoarylalkynyl (5–20C);
$R_e$ is H or a protecting group or is mono- or disubstituted amino carbonyl;
$R_f$ is H; substituted or unsubstituted alkyl (1–10C); substituted or unsubstituted alkenyl (1–10C); substituted or unsubstituted alkynyl (1–10C); substituted or unsubstituted aryl (4–14C); substituted or unsubstituted arylalkyl (5–20C); or —$OR_f$ may be replaced by —H;
one of Z and Y is H and the other is OH or protected OH, or is amino, mono- or dialkyl-amino, protected amino, or an aminoheterocycle or
Z and Y together are =O, =NOH or a derivatized oxime;
including any pharmaceutically acceptable salts thereof and any stereoisomeric forms and mixtures of stereoisomeric forms thereof, are antimicrobial agents.

27 Claims, 6 Drawing Sheets

U.S. PATENT DOCUMENTS

| | | | |
|---|---|---|---|
| 5,527,780 A | 6/1996 | Agouridas et al. | 514/29 |
| 5,635,485 A | 6/1997 | Agouridas et al. | 514/29 |
| 5,672,491 A | 9/1997 | Khosla et al. | |
| 5,747,467 A | 5/1998 | Agouridas et al. | 514/29 |
| 5,750,510 A | 5/1998 | Elliott et al. | |
| 5,770,579 A | 6/1998 | Agouridas et al. | 514/29 |
| 5,866,549 A | 2/1999 | Or et al. | 514/29 |
| 6,022,965 A | 2/2000 | Benedetti et al. | 536/125 |
| 6,043,226 A * | 3/2000 | Lundy et al. | 514/29 |
| 6,066,721 A | 5/2000 | Khosla et al. | |
| 6,080,555 A | 6/2000 | Khosla et al. | |
| 6,121,432 A | 9/2000 | Bonnet et al. | 536/7.2 |
| 6,124,269 A | 9/2000 | Phan et al. | 514/29 |
| 6,271,255 B1 | 8/2001 | Leadlay et al. | 514/450 |
| 6,274,560 B1 | 8/2001 | Khosla et al. | 514/29 |
| 6,274,715 B1 | 8/2001 | Or et al. | 536/7.4 |

FOREIGN PATENT DOCUMENTS

| | | |
|---|---|---|
| WO | 97/02358 | 1/1997 |
| WO | 98/01546 | 1/1998 |
| WO | 98/01571 | 1/1998 |
| WO | 98/09978 | 3/1998 |
| WO | 99/03986 | 1/1999 |
| WO | 99/21871 | 5/1999 |
| WO | 99/35157 | 7/1999 |
| WO | 00/26224 | 5/2000 |
| WO | 00/26349 | 5/2000 |
| WO | 00/34297 | 6/2000 |
| WO | 00/44761 | 8/2000 |
| WO | 00/71557 | 11/2000 |

* cited by examiner

Post-PKS Biosynthesis of Erythromycins

MACROLIDE ANTIINFECTIVE AGENTS

This application claims priority under 35 U.S.C. §119 from U.S. provisional patent application Ser. No. 60/129,729 filed Apr. 16, 1999, No. 60/172,154 filed Dec. 17, 1999, No. 60/140,175 filed Jun. 18, 1999, No. 60/172,159 filed Dec. 17, 1999, No. 60/173,805 filed Dec. 30 1999, and No. 60/173,804 filed Dec. 30, 1999, and a continuation U.S. utility patent application Ser. No. 09/550,045 filed on Apr. 14, 2000 entitled "Macrolide Antiinfectives". The contents of these applications are relied on and incorporated herein in their entirety by reference.

TECHNICAL FIELD

The invention is directed to antibacterial compounds that expand the repertoire of erythromycin-like antibiotics. More particularly, the invention concerns macrolide antibiotics containing an erythronolide nucleus modified at least at the substituent at C-13.

BACKGROUND ART

The increasing number of microbial strains that have acquired resistance to the currently available known antibiotic compounds is recognized as a dangerous threat to public health. As the use of such compounds has proliferated, so too has the need for expanding the options available to treat a wide variety of microbial-based conditions. The need for a larger choice of antimicrobial compounds extends beyond treatment of human infection and to a need to preserve food and other perishable commodities. New antibiotics can also be essential for resistant plants and animals as well as to provide resistance to materials that otherwise are subject to microbially caused corrosion.

Thus, there is a clear need for an expanded armament of compounds which can provide a multifaceted defense against unwanted microbial activity.

WO 98/09978 published Mar. 12, 1998 and incorporated herein by reference discloses modified forms of erythromycin which lack a cladinose residue at the 3-position and which are derivatized in various ways in positions 9–12 of the macrolide ring. Similarly, U.S. Pat. No. 5,750,510, issued May 12, 1998 and incorporated herein by reference, discloses modified erythromycin derivatives.

The naturally occurring erythromycins have the structure

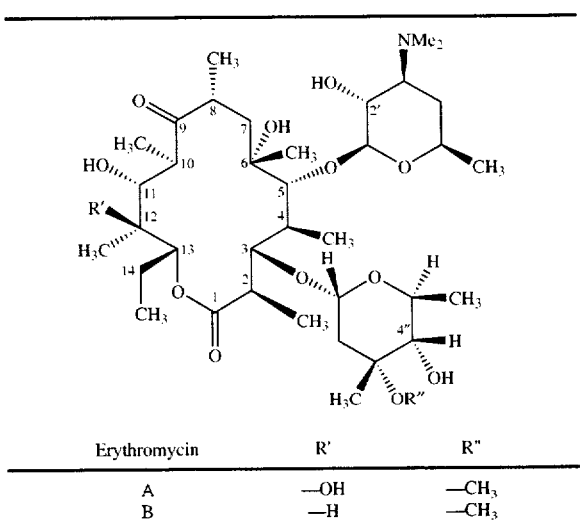

| Erythromycin | R' | R" |
|---|---|---|
| A | —OH | —CH$_3$ |
| B | —H | —CH$_3$ |

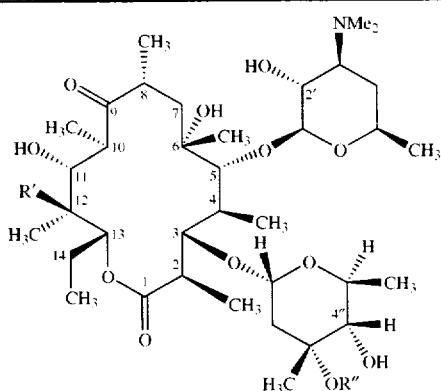

| Erythromycin | R' | R" |
|---|---|---|
| C | —OH | —H |
| D | —H | —H | wherein R' can be H or OH and R" can be H or CH$_3$.

All of the compounds disclosed in the above-referenced patent documents contain an ethyl group at position 13 of the macrolide ring. The present inventors have found that alterations in the substituent at position 13 results in a large number of compounds with excellent antibacterial activity.

DISCLOSURE OF THE INVENTION

The invention is directed to erythronolide derivatives that contain modifications from the native structure. All of the compounds of the invention are modified at least at position 13.

Thus, in one aspect, the invention is directed to compounds of the formula

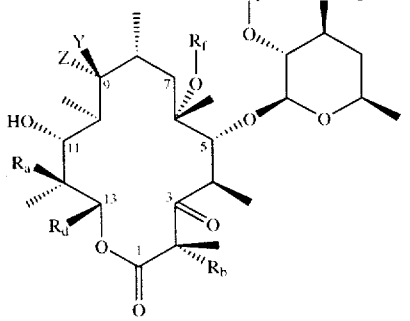

(1)

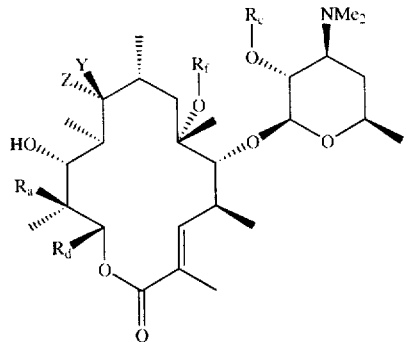

(2)

-continued
or

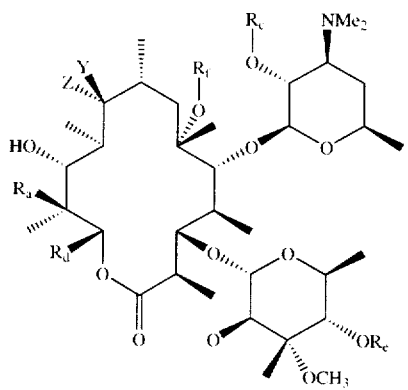

(3)

or the 10,11-anhydro forms thereof; wherein $R_a$ is H or OH, preferably OH;

$R_b$ is H or halogen;

$R_c$ is H or a protecting group;

$R_d$ is methyl; unsubstituted alkyl (3–10C); substituted alkyl (1–10C); substituted or unsubstituted alkenyl (2–10C); substituted or unsubstituted alkynyl (2–10C); substituted or unsubstituted aryl (4–14C); substituted or unsubstituted arylalkyl (5–20C); substituted or unsubstituted arylalkenyl (5–20C); substituted or unsubstituted arylalkynyl (5–20C); substituted or unsubstituted amidoarylalkyl (5–20C); substituted or unsubstituted amidoarylalkenyl (5–20C); or substituted or unsubstituted amidoarylalkynyl (5–20C);

$R_e$ is H or a protecting group or is mono- or disubstituted amino carbonyl;

$R_f$ is H; substituted or unsubstituted alkyl (1–10C); substituted or unsubstituted alkenyl (1–10C); substituted or unsubstituted alkynyl (1–10C); substituted or unsubstituted aryl (4–14C); substituted or unsubstituted arylalkyl (5–20C); or $OR_f$ may be replaced by H;

one of Z and Y is H and the other is OH or protected OH, or is amino, mono- or dialkyl-amino, protected amino, or an aminoheterocycle or Z and Y together are =O, =NOH or a derivatized oxime;

including any pharmaceutically acceptable salts thereof and any stereoisomeric forms and mixtures of stereoisomeric forms thereof.

In another aspect, the invention is directed to pharmaceutical or preservative compositions containing the compounds of formulas (1)–(3) and to methods to treat infectious diseases by administering these compounds or to preserve materials by providing them.

The compounds of the invention have antibiotic activity, but preferably are useful as semi-synthetic intermediates for forming 10, 11 anhydro forms of the compounds that are further converted to compounds having an erythronolide nucleus and having a ring between the C10 and C11 positions of the erythronolide nucleus as described in U.S. provisional patent application Ser. No. 60/140,175 filed Jun. 18, 1999 and No. 60/172,159 filed Dec. 17, 1999 and U.S. utility patent application Ser. No. 09/550,045 filed Apr. 14, 2000 entitled "Macrolide Antiinfectives", which are incorporated by reference.

A BRIEF DESCRIPTION OF THE DRAWINGS

MODES OF CARRYING OUT THE INVENTION

The compounds of the invention are conveniently synthesized by combining synthetic chemical techniques with microbiological processes involving genetically engineered microorganisms. Briefly, in a preferred mode of carrying out the invention, a microbial host, preferably a host which does not itself produce a macrolide antibiotic, is provided with a recombinant expression system for the production of modified 6-deoxyerythronolide B (6-dEB), which expression system in some instances will have been altered by a disruption in the catalytic domain of the ketosynthase moiety in the first module. For substituents in which $R_d$ is methyl, host cells are used which do not have a disrupted domain of the ketosynthase moiety. This alteration in the 6-dEB polyketide synthase (PKS) results in the inability of this PKS to utilize its native starter unit, and thus permits inclusion of a synthetic diketide thioester for its initial condensation product in the sequence of reactions leading to modified 6-dEB without competition from the diketide that would otherwise, natively, have been produced. Thus, the recombinant host can be provided a synthetic diketide thioester for incorporation into the resulting polyketide. The incorporation of this diketide into the resulting polyketide results in a polyketide with a substituent at position 13 that may be selected as desired. Preferred methods for preparing the synthetic polyketide thioesters are set forth in copending application U.S. Ser. No. 60/117,384 filed Jan. 27, 1999 and Ser. No. 09/492,733 filed on Jan. 27, 2000, which are incorporated herein by reference.

Recombinant forms of the 6-dEB PKS containing inactivated ketosynthase (KS) domains in the first module (KS1) and appropriate organisms modified to contain an expression system for this PKS are described in PCT applications WO 97/02358, published Jan. 28, 1997 and WO 99/03986, published Jan. 28, 1999, incorporated herein by reference.

Additional manipulations which provide alternative substituents on the macrolide ring are disclosed in U.S. Ser. No. 09/073,538 filed May 6, 1998, No. 60/129,731 filed Apr. 16, 1999, and Ser. No. 09/429,349 filed Oct. 28, 1999 and are incorporated herein in their entirety by reference.

The polyketide resulting from expression of the modified PKS is then isolated and purified, if desired, from the recombinantly modified organism and fed to *Saccharopolyspora erythraea*, which contains the functionality for postpolyketide modifications, including glycosylation. Other modifications include hydroxylation at positions 6 and/or 12. The resulting modified erythromycin is then isolated and chemically modified to obtain the compounds of the invention. Synthetic methods for providing these modifications are described in WO 98/09978 and U.S. Pat. No. 5,750,510, referenced hereinabove.

Figure 1:
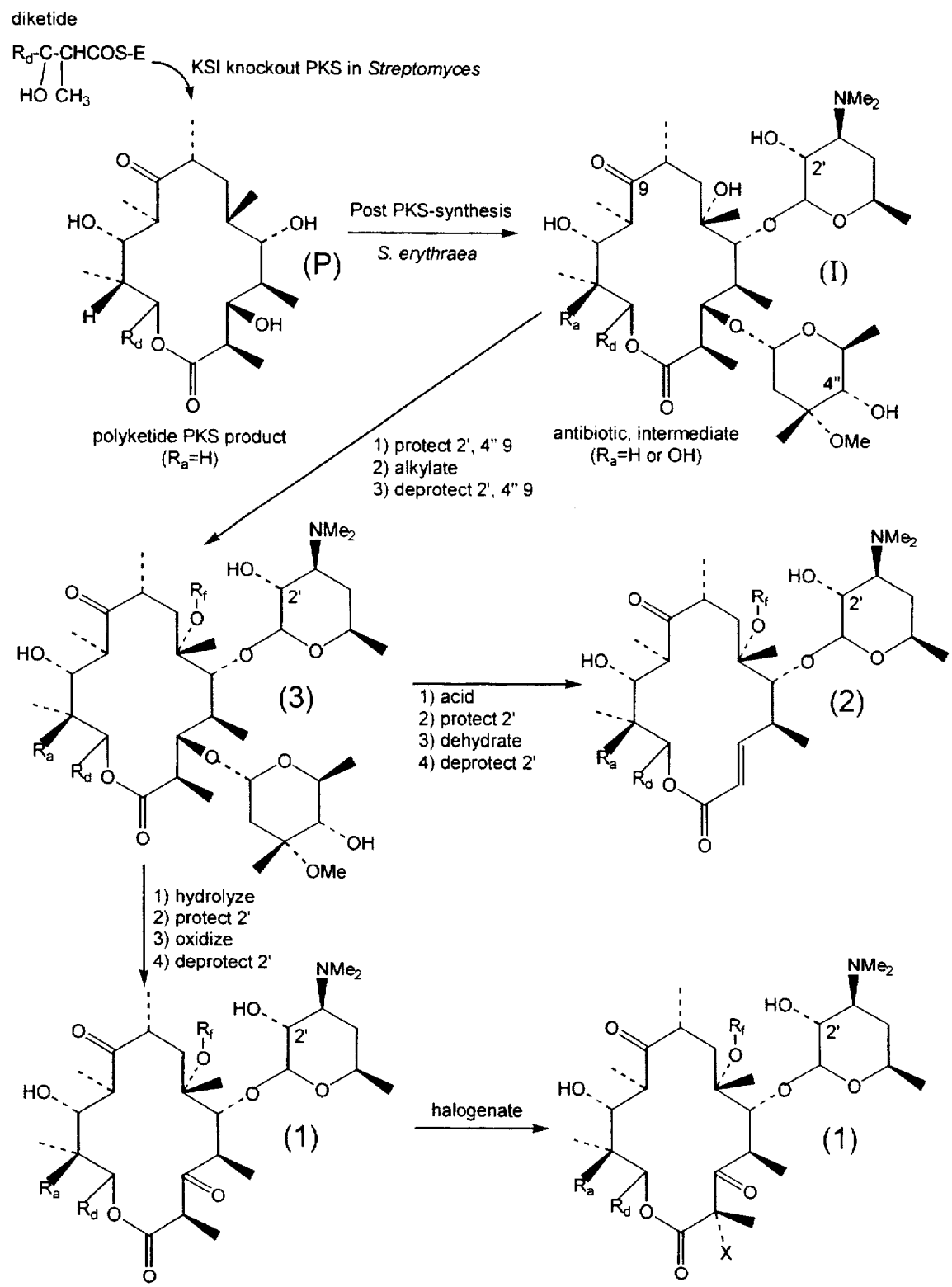
FIG. 1 shows a schematic of the synthesis of the compounds of the invention.
Figure 2:
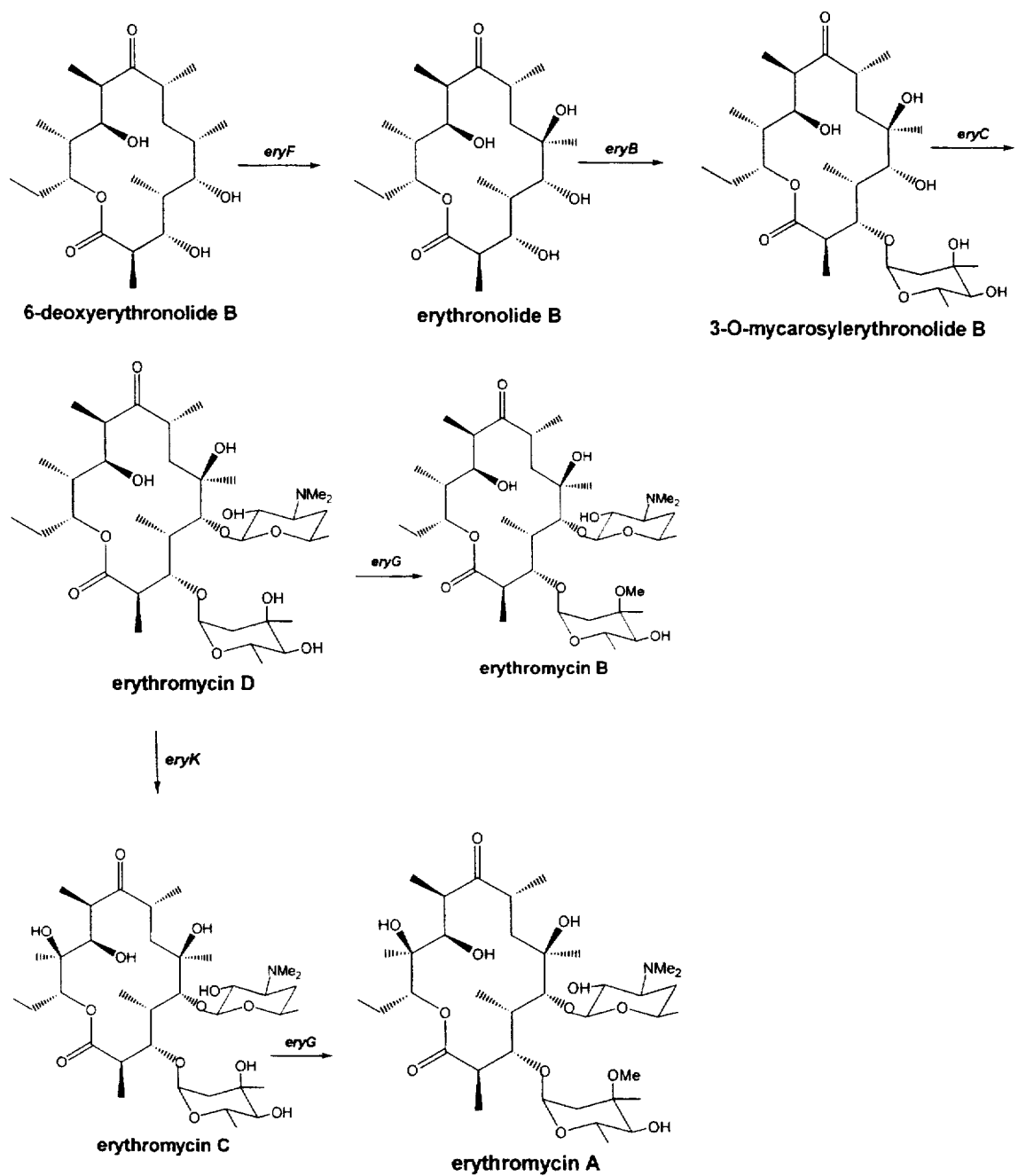
FIG. 2 shows the post-PKS biosynthesis of erythromycins. This pathway is employed in the present invention, as shown in FIG. 1.

The general method for synthesizing compounds of the invention is shown in FIG. 1.

The resulting Antiinfectives compound is active in vitro and in vivo for activity against a panel of representative microorganisms. The compounds of the invention thus exhibit a sufficient diversity in specificity to cover the spectrum of antibiotic activities desired.

For use in treating infectious disease, the compounds of the invention are formulated into suitable compositions which will include typical excipients, pharmaceutically acceptable counterions if the compound is a salt, further additives as desired, such as antioxidants, buffers, and the like, and administered to animals or humans. The types of formulations that are appropriate for these compounds are similar to those for the macrolide antibiotics in general. Formulations may be found, for example, in *Remington's Pharmaceutical Sciences*, Mack Publishing Co., latest edition. The compounds can be administered by any desired route, including injection, oral administration, transdermal administration, transmucosal administration, or any combination. The compounds of the invention can also be administered with additional active ingredients if desired.

The compounds of the invention are of formulas (1)–(3) as set forth above, as well as any stereoisomeric forms of these compounds as shown. The particular stereoisomers depicted are those resulting from the preferred method of synthesis set forth above and exemplified herein; however, by modifying the expression system for the PKS, or by altering the chirality of the diketide, or by synthetic chemical conversion, other stereoisomers may also be prepared. Additional chiral centers may be present in the substituents, such as $R_d$ and $R_f$. The stereoisomers may be administered as mixtures, or individual stereoisomers may be separated and utilized as is known in the art.

The properties of the compounds of formulas (1)–(3) are defined by the substituents $R_a$–$R_f$, Y and Z. Preferred embodiments of these substituents are set forth hereinbelow. They contain moieties which are defined as follows:

"Halogen" includes fluoro, chloro, bromo and iodo, and most preferably fluoro.

"Alkyl" refers to a saturated straight-chain, branched chain or cyclic hydrocarbyl moiety containing a specified number of carbons and that may contain one or more suitable heteroatoms; similarly, alkenyl and alkynyl refer to straight or branched chain or cyclic hydrocarbon substituents containing one or more double bonds or one or more triple bonds, respectively, and containing one or more suitable heteroatoms.

"Aryl" refers to an aromatic substituent that may contain one or more suitable heteroatoms such as phenyl, naphthyl, quinolyl, or phenanthryl.

"Arylalkyl," "arylalkenyl," or "arylalkynyl" refer to substituents wherein an aryl group is linked to the substituted moiety through an alkyl, alkenyl or alkynyl linkage, respectively. Again, the number of carbons in the arylalkyl, arylalkenyl or arylalkynyl groups will be specified.

"Amidoarylalkyl," "amidoarylalkenyl," or "amidoarylalkynyl" refer to substituents wherein an aryl group is linked to the substituted moiety through an amido and an alkyl, alkenyl or alkynyl linkage, respectively. Again, the number of carbons in the amidoarylalkyl, amidoarylalkenyl or amidoarylalkynyl groups will be specified.

Thus, included among the defined substituents herein are "heteroalkyl," "heteroalkenyl," "heteroalkynyl," "heteroaryl," "heteroarylalkyl," and the like. Suitable heteroatoms include N, O, and S.

All of the foregoing substituents may be unsubstituted or may be further substituted. Typical substituents include R, —OR, —SR, —NR$_2$, —COR, —COOR, —CONR$_2$, —OOCR, —NRCOR, —OCONR$_2$, —CN, —CF$_3$, —NO$_2$, —SOR, —SO$_2$R, halogen, wherein each R is independently H or is alkyl, alkenyl, alkynyl, aryl, arylalkyl, or the hetero forms of these as defined above. In addition, alkyl, alkenyl and alkynyl may be substituted by aryl or heteroaryl, which may, themselves, be further substituted. Aryl and heteroaryl may also be substituted by alkyl, alkenyl or alkynyl, or by additional aryl or heteroaryl moieties.

"A derivatized oxime" is of the formula =N—O—R, wherein R is other than H and is otherwise defined as above.

A "protecting group" for a hydroxy includes acyl groups, silyl groups, and the like. Suitable protecting groups are described by Greene, T. W., et al., in *Protecting Groups in Organic Synthesis*, 2$^{nd}$ Ed., John Wiley & Sons, Inc. (1991), incorporated herein by reference.

The invention includes more preferred embodiments of the compound defined above. $R_d$ is preferably butyl, pentyl, methoxyethoxymethyl, isobutyl, methylcyclohexyl, phenyl, benzyl, ethylphenyl, 3-(benzyloxy)propyl, 2-(pyrimidin-2-ylthio)ethyl, propyl, fluoroethyl, chloroethyl, vinyl, 3-butenyl, or azidoethyl and more preferably propyl, fluoroethyl, chloroethyl, vinyl, 3-butenyl, or azidoethyl. U.S. Ser. No. 60/117,384 filed Jan. 27, 1999 and U.S. Ser. No. 09/492,733 filed Jan. 27, 2000 both of which are incorporated herein by reference describe various oligoketide thioesters, preferably diketide thioesters, that can be incorporated at the C-13 position. Such diketide thioesters as described therein are incorporated into the compounds of the invention and thus determine preferred $R_d$ groups at the C-13 position.

In another preferred embodiment, $R_f$ is H or lower C1–C3 alkyl, and more preferably methyl. $R_f$ is also preferably arylalkenyl or arylalkynyl such as 3-arylprop-2-enyl or 3-arylprop-2-ynyl. Preferably the aryl group in the preferred arylalkenyl or arylalkynyl embodiments are 3-quinolyl, 4-quinolyl, 5-quinolyl, phenyl, 4-fluorophenyl, 4-chlorophenyl, 4-methoxyphenyl, 6-quinolyl, 6-quinoxalyl, 6-amino-3-quinolyl, or 4-isoquinolyl.

Synthesis of the Invention Compounds

As described above, the antibiotic starting materials for any further chemical synthesis to obtain the compounds of the invention are prepared, preferably, by feeding a suitable diketide to a microorganism modified to contain an expression system for the 6-dEB PKS containing a KS1 knockout, or by a host cell that provides a methyl at the 13-position, followed by feeding the resulting polyketide to a recombinant strain of *Saccharopolyspora erythraea* that has been altered to eliminate production of 6-dEB. A strain can be prepared that is able to hydroxylate either both the 6- and 12-positions or the 12-position only. In this case, —OR$_f$ is replaced by —H. Alternatively, a strain can be prepared that hydroxylates only the 6-position. The recombinant *S. erythraea* strain, K40-67, is obtained by transforming an *S. erythraea* strain that produces high levels of erythromycin A with a plasmid comprising a mutated eryA1 sequence encoding an inactivated KS1 domain. By homologous recombination, the resulting transformants now are unable to produce 6-dEB as a competitor to the fed polyketide and, instead, hydroxylate the 6-position and 12-position and glycosylate the 3-position and 5-position of the modified polyketide that has been made in Streptomyces or other polyketide-producing transformant. If a macrolide having only the 12-position, and not the 6-position hydroxylated is desired (OR$_f$ is replaced by H), an *S. erythraea* strain is constructed by disrupting the eryF hydroxylase gene in strain K40-67. Alternatively, the eryK gene can be disabled, wherein embodiments of compounds (1)–(3) wherein R$_a$ is H may readily be produced.

The glycosylation reactions for the production of the erythromycins result in the diglycosylated forms analogous to the naturally occurring erythromycins. If the compounds of formula (3) are to be prepared from the initial product, the hydroxyl group of the cladinose ring (attached to position 3)

may then need to be protected for subsequent modification of the macrolide substituents.

The modified erythromycins of the invention, in addition to modification at C-13, may contain an —OH group at position 6, unless $OR_f$ is replaced by H as described above. To construct the compounds of formulas (1), (2) and (3) where position 6 is $OR_f$, the compound of formula (3) is provided with protecting groups which form one embodiment of $R_c$ and $R_c$. Such protection is effected using suitable protecting reagents such as acetic anhydride, benzoic anhydride, benzochloro formate, hexamethyldisilazane, or a trialkylsilyl chloride in an aprotic solvent. Aprotic solvents include, for example, dichloromethane, chloroform, tetrahydrofuran, N-methyl pyrrolidone, dimethyl sulfoxide (DMSO), dimethyl formamide (DMF) and the like. Mixtures may also be used. Protection of both sugar hydroxyls in formula (3) may be done simultaneously or sequentially.

In addition to protecting the 2' and 4" hydroxyl groups of the two glycose residues, the keto group at position 9 of the macrolide ring must also be protected. Typically, this is effected by converting the keto group to a derivatized oxime. Particularly preferred embodiments for R in the formula =NOR include unsubstituted or substituted alkyl (1-12C), substituted or unsubstituted aryl (6-10C), alkyl (1-12C), substituted or unsubstituted heteroaryl (6-10C), alkyl (1-12C), and heteroalkyl (such as substituents of the formula $CR'_2OR$ wherein each R', in addition to being independently embodied as R as set forth above, may, together with the other, form a cycloalkyl ring (3-12C)). A preferred derivatized oxime is of the formula =NOR wherein R is isopropoxycyclohexyl.

With the 9-keto group and the 2' and 4" hydroxyls protected, it is then possible to alkylate the 6-hydroxy group in the precursor to the compound of formula (3) by reaction with an alkylating agent in the presence of base. Alkylating agents include alkyl halides and sulfonates. For example, the alkylating agents may include methyl tosylate, 2-fluoroethyl bromide, cinnamyl bromide, crotonyl bromide, allyl bromide, propargyl bromide, and the like. The alkylation is conducted in the presence of base, such as potassium hydroxide, sodium hydride, potassium isopropoxide, potassium t-butoxide, and an aprotic solvent.

Especially preferred for $R_f$ are methyl, allyl and ethyl.

Once the alkylation of the 6-hydroxyl is completed, the sugar residues and the macrolide ring may be deprotected. Deprotection of the glycoside moieties is conducted as described by Green, T. W., et al., in *Protective Groups in Organic Synthesis*, infra. Similar conditions result in converting the derivatized oxime to =NOH. If formation of the underivatized oxime is not concurrent with deprotection, the conversion to the oxime is conducted separately.

The oxime can then be removed and converted to a keto group by standard methods known in the art. Deoximating agents include inorganic sulfur oxide compounds such as sodium hydrogen sulfite, sodium pyrosulfate, sodium thiosulfate, and the like. In this case, protic solvents are used, such as water, methanol, ethanol, isopropanol, trimethyl silanol and mixtures of these. In general, the deoximation reaction is conducted in the presence of an organic acid.

At this point in the process, or later, after the compound of formula (3) has been converted to the compounds of formulas (1) or (2) as further described below, the group introduced at the 6-hydroxyl can further be manipulated. Conveniently, the initial substitution may provide a 6-O-allyl—i.e., $O$—$CH_2CH$=$CH_2$—which can further be derivatized by reduction to give the 6-O propyl compound, or be treated with osmium tetroxide to provide the 2,3-dihydroxypropyl compound, which can further be esterified at each oxygen atom. The O-allyl derivative can also be oxidized with m-chloroperoxybenzoic acid in an aprotic solvent to provide the epoxy compound which can be opened with amines or N-containing heteroaryl compounds to provide compounds with N-containing side-chains, or can be oxidized under Wacker conditions to provide the substituent $O$—$CH_2$—$C(O)$—$CH_3$, or can be ozonized to provide the aldehyde. The aldehyde can then be converted to the oxime or reacted with a suitable amine and reduced in the presence of a borohydride reducing agent to provide an amine. The oxime can also be converted to a nitrile by reaction with a dehydration agent in an aprotic solvent. The O-allyl derivative can also be reacted with an aryl halide under Heck conditions (Pd(II) or Pd(O), phosphine and amine or inorganic base) to provide a 3-aryl prop-2-enyl derivative. This derivative can then be reduced with hydrogen and palladium on carbon to provide a 3-arylpropyl derivative. If the initial substituent $R_f$ is a 2-propyne, similar reactions can be employed to provide alterations in the side-chain, including arylation.

In order to convert the compound of formula (3) into the compound of formula (1), by first removing the cladinose moiety, the compound of formula (3) is treated with mild aqueous acid or with a deglycosylating enzyme. Suitable acids include hydrochloric, sulfuric, chloroacetic, trifluoroacetic and the like, in the presence of alcohol. Reaction times are typically 0.5–24 hours at a temperature of −10–35° C. During this reaction, the 2' group of the remaining sugar is protected as set forth above and deprotected subsequent to the decladinizing reaction. The resulting hydroxyl group at the 3-position of the macrolide ring is then oxidized to the ketone using a modified Swern oxidation procedure. In this procedure, an oxidizing agent such as N-chlorosuccinimide-dimethyl sulfide or a carbodiamide-dimethylsulfoxide is used. Typically, a compound of formula (3) is added to pre-formed N-chlorosuccinimide and dimethyl sulfide complex in a chlorinated solvent such as methylene chloride at −10–25° C. After being stirred for 0.5–4 hours, a tertiary amine such as triethylamine is added to produce the corresponding ketone and the 2' protecting group is then removed.

In order to halogenate the macrolide at position 2 (converting $R_b$ is H to halogen), the compound of formula (1) is treated with a base and an electrophilic halogenating reagent such as pyridinium perbromide or N-fluorobenzenesulfonimide. The position 2 can be halogenated at any time after the 3 keto compound is prepared.

The appropriate substituent such as vinyl, ethenyl, butenyl or azido at the C-13 position can be further manipulated. For example, an amidoacetate salt of the compound of the invention can be derivatized using an arylacetyl chloride to yield an arylamino alkyl group on the C-13 position. Preferably the C13 derivatives of an azido group take place before the ketolide is formed. Derivations of an ethenyl group can take place either before or after the ketolide is formed.

In order to obtain the compounds of formula (2), the compound resulting from the deglycosylation reaction of formula (1) is treated with a dehydrating agent such as carbonyl diimidazole and base.

In order to prepare compounds of formulas (1)–(3) wherein one of Z and Y is H and the other OH or protected OH or is an amino derivative as described above, either the carbonyl or oxime or derivatized oxime is reduced using a suitable reducing agent, such as sodium borohydride, Raney nickel/$H_2$, or reductive amination with the use of sodium cyanoborohydride and an amine. Substituted amines can also be obtained by alkylation.

Novel methods of synthesis of the compounds of the invention are also provided.

EXEMPLARY EMBODIMENTS

The compounds of formulas (1), (2) and (3) are defined by their various substituents. Table 1 illustrates compounds within the scope of the present invention which are:

of formula (1) wherein $R_a$ is H or OH, $R_b$ is H, Cl, or F, and $R_c$ is H;

of formula (2) wherein $R_a$ is H or OH and $R_c$ is H; and of formula (3) wherein $R_a$ is H or OH, $R_c$ is H, and $R_e$ is H, or a radical a, b, c, or d:

TABLE 1

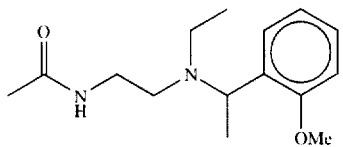
(a):

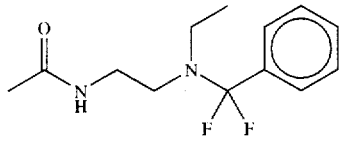
(b):

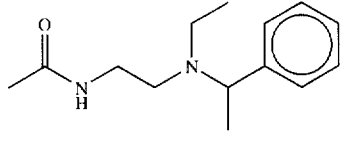
(c):

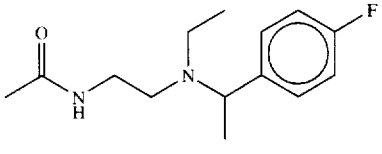
(d):

| Rd | Rf | Y | Z |
|---|---|---|---|
| —CH₃ | —CH₂CH₂-φ | =O | |
| —CH=CH₂ | —CH₂CH=CH-φ | =O | |
| —CH₂CH₂CH₃ | —CH₂CH₂NHCH₃ | =NOH | |
| —CH₃ | —CH₂CHOHCH₃ | =NOCH₂CH₃ | |
| —CH(CH₃)₂ | —CH₂-φ | H | OH |
| —CH₃ | —CH₂—CH=CH₂ | =O | |
| —CH₃ | —CH₂—CH=CH-(3-quinolyl) | =O | |
| —CH₃ | —CH₂—CH₂—CH₂-(3-quinolyl) | =O | |
| —CH₃ | —CH₂—CH=CH-(2-methyl-6-quinolyl) | =O | |
| —CH₃ | —CH₂—CH=CH-(5-isoquinolyl) | =O | |
| —CH₃ | —CH₂—CH=CH-(3-bromo-6-quinolyl) | =O | |
| —CH₃ | —CH₂—C=CH-(6-methoxy-2-naphthyl) | =O | |
| —CH₃ | —CH₂—C≡C-(2-phenylethenyl) | =O | |
| —CH₃ | —CH₂—C≡C-(3-quinolyl) | =O | |
| —CH₃ | —CH₂—C≡C-naphthyl | =O | |
| —CH₃ | —CH₂—C≡C-(6-methyl-2-naphthyl) | =O | |
| —CH₃ | —CH₂—C≡C-(3-(2-furanyl)-6-quinolyl) | =O | |
| —CH=CH₂ | —CH₃ | =O | |
| —CH₂OH | —CH₂—C=CH-(4-fluorophenyl) | =O | |
| —CH₂OH | —CH₂—C=CH-(3-quinolyl) | =O | |
| —CH₂OH | —CH₂—C=CH-(6-quinolyl) | =O | |
| —CH₂OCH₃ | —CH₂—C=CH-(3-pyridyl) | =O | |
| —CH₂CH₂CH₃ | —CH₂—C=CH-(3-quinolyl) | =O | |
| —CH₂CH₂CH₃ | —CH₂—C=CH-(6-chloro-3-quinolyl) | =O | |
| —CH₂CH₂CH₃ | —CH₂—C=CH-(4-quinolyl) | =O | |
| —CH₂CH₂CH₃ | —CH₂—C=CH-(6-chloro-3-quinolyl) | =O | |
| —CH₂CH₂CH₃ | —CH₂—C=CH-(6-hydroxy-3-quinolyl) | =O | |
| —CH₂CH₂CH₃ | —CH₂—C=CH-(6-methoxy-3-quinolyl) | =O | |
| —CH₂CH₂CH₃ | —CH₂—C=CH-(6-aminocarbonyl-3-quinolyl) | =O | |
| —CH₂CH₂CH₃ | —CH₂—C=CH-(3-(2-thiophenyl)-6-quinolyl) | =O | |
| —CH₂CH₂CH₃ | —CH₂—C=CH-(6-hydroxy-2-naphthyl) | =O | |
| —CH₂CH₂CH₃ | —CH₂—C≡C-(3-quinolyl) | =O | |
| —CH₂CH₂CH₃ | —CH₂—C≡C-(6-chloro-2-naphthyl) | =O | |
| —CH₂CH₂CH₃ | —CH₂—C≡C-(6-quinolyl) | =O | |
| —CH₂CH₂CH₃ | —CH₂CH₂NHCH₂CH₂-(2-chlorophenyl) | =O | |
| —CH₃ | —CH₂CH₂NH₂ | =O | |
| —CH₃ | ORf replaced by H | —NH₂ | H |
| —CH₃ | —CH₃ | —NH₂ | H |

TABLE 1-continued
(a): 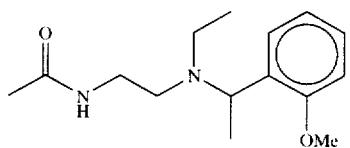
(b): 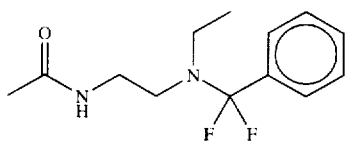
(c): 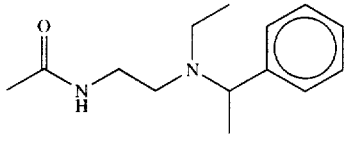
(d): 
| Rd | Rf | Y | Z |
|---|---|---|---|
| —CH$_3$ | OR$_f$ replaced by H |  piperazinyl | H |
| —CH$_3$ | OR$_f$ replaced by H | piperidinyl | H |
| —CH$_3$ | OR$_f$ replaced by H | morpholinyl | H |
| —CH$_3$ | —CH$_2$CHClCH$_3$ | H | piperazinyl |
| —CH$_3$ | —CH$_2$CHClCH$_3$ | H | piperidinyl |
| —CH$_3$ | —CH$_2$CHClCH$_3$ | H | morpholinyl |
| —CH$_3$ | —CH$_3$ | piperazinyl | H |
| —CH$_2$CH$_2$CH$_3$ | OR$_f$ replaced by H | H | piperazinyl |
| —CH$_2$CH$_2$CH$_3$ | OR$_f$ replaced by H | —NH$_2$ | H |

TABLE 1-continued (a):

[Structure: acetamide-NH-CH2CH2-N(ethyl)-CH(CH3)-phenyl(2-OMe)]

(b):

[Structure: acetamide-NH-CH2CH2-N(ethyl)-CF2-phenyl]

(c):

[Structure: acetamide-NH-CH2CH2-N(ethyl)-CH(CH3)-phenyl]

(d):

[Structure: acetamide-NH-CH2CH2-N(ethyl)-CH(CH3)-phenyl(4-F)]

| Rd | Rf | Y | Z |
|---|---|---|---|
| —CH$_2$CH$_2$CH$_3$ | —CHCH(OCH$_3$)CH$_3$ | —N⟨piperazine⟩NH | H |
| —CH$_2$CH$_2$CH$_3$ | —CH$_3$ | H | —N⟨piperazine⟩NH |
| —CH$_2$CH$_2$CH$_3$ | —CH$_2$CH$_2$CH$_3$ | —N⟨piperidine⟩ | H |
| —CH$_2$CH$_2$CH$_3$ | —CH$_2$CHBrCH$_3$ | H | —N⟨piperidine⟩ |
| —CH$_3$ | —CH$_2$CHOHCH$_3$ | =NOCHCH$_3$ | |
| —CH$_2$CH$_2$CH$_3$ | —CH$_2$CH$_2$CH$_3$ | —NH$_2$ | H |

EXAMPLES

The following examples are intended to illustrate but not to limit the invention.

Compound numbers and designations are found in Illustrative Scheme 1.

In these examples, in the first general step of the method, a 6-deoxyerythronolide B (6-dEB) derivative compound is prepared by fermentation of a recombinant Streptomyces host cell.

The fermentation to produce 15-methyl-6-deoxyerythronolide B and 14,15-dehydro-6-deoxyerythronolide B requires a synthetic diketide intermediate to be fed to the fermenting cells. The preparation of these synthetic diketides is described in Example 1. These synthetic diketides are substrates for a 6-deoxyerythronolide B synthase (DEBS) that is unable to act on its natural substrate (propionyl CoA) due to a mutation in the ketosynthase domain of module 1 of DEBS. This recombinant DEBS is provided by plasmid pJRJ2 in *Streptomyces coelicolor* CH999. *S. coelicolor* CH999 is described in U.S. Pat. No. 5,672,491, incorporated herein by reference. A derivative of *S. coelicolor* CH999, *S. coelicolor* K39-02, that has been genetically modified to include aptpA gene, is described in U.S. patent application Ser. No. 09/181,833, incorporated herein by reference can also be employed for this purpose.

Plasmid pJRJ2 encodes the eryAI, eryAII, and eryAIII genes; the eryAI gene contained in the plasmid contains the KS1 null mutation. The KS1 null mutation prevents formation of the 6-deoxyerythronolide B produced by the wild-type gene unless exogenous substrate is provided. Plasmid pJRJ2 and a process for using the plasmid to prepare novel 13-substituted erythromycins are described in PCT publication Nos. 99/03986 and 97/02358 and in U.S. patent application Ser. No. 08/675,817, filed Jul. 5, 1996; Ser. No. 08/896,323, filed Jul. 17, 1997; and Ser. No. 09/311,756, filed May 14, 1999, each of which is incorporated herein by reference. The exogenous substrates provided can be prepared by the methods and include the compounds described in PCT patent application No. PCT/US00/02397 and U.S. patent application Ser. No. 09/492,733, both filed Jan. 27, 2000, by inventors G. Ashley et al., and both of which claim priority to U.S. patent application Ser. No. 60/117,384, filed Jan. 27, 1999, each of which is incorporated herein by reference. PKS genes other than the ery genes can also be employed; suitable genes include the KS1 null mutation containing oleandolide and megalomicin PKS genes described in U.S. patent application Ser. No. 60/158,305, filed Oct. 8, 1999 and Ser. No. 09/428,517, filed Oct. 28, 1999, and PCT application No. US99/24478, filed Oct. 22, 1999, each of which is incorporated herein by reference.

The fermentation to produce 14-nor-6-deoxyerythronolide B does not require diketide feeding, because the desired compound is produced by the recombinant host cell *Streptomyces coelicolor* CH999/pCK7. Plasmid pCK7 is described in U.S. Pat. No. 5,672,491 and comprises the DEBS genes. A derivative of plasmid pCK7, pKOS011-26, can also be used. The host cell comprising pKOS011-26 and a recombinant ptpA gene is *S. coelicolor* 27-26/pKOS011-26. These host cells produce both 6-deoxyerythronolide B and 14-nor-6-deoxyerythronolide, due to the incorporation of propionyl CoA and acetyl CoA, both of which serve as substrates for DEBS.

The fermentation of *Streptomyces coelicolor* CH999/pJRJ2 and *S. coelicolor* CH999/pCK7 is described in Example 2. The isolation of the 6-deoxyerythronolide products resulting from this fermentation can be achieved by separation.

The isolated products are then added to the fermentation broth of *Saccharopolyspora erythraea* strains to make other useful intermediate compounds of the invention. The *S. erythraea* strains catalyze the biosynthesis and attachment of sugar residues to the 3 and 5 positions of the 6-dEB derivative compounds. These strains also comprise a functional eryK gene product and so hydroxylate the 6-dEB derivative compounds at the 12 position. The strains differ in regard to whether a functional eryF gene product is produced. If so, then the compounds produced are hydroxylated at the 6 position as well. If not, then a 6-deoxyerythromycin A derivative is produced. These *S. erythraea* fermentations are described in Example 3, together with the isolation of the erythromycin A derivative compounds from the fermentation broth.

Figure 3:
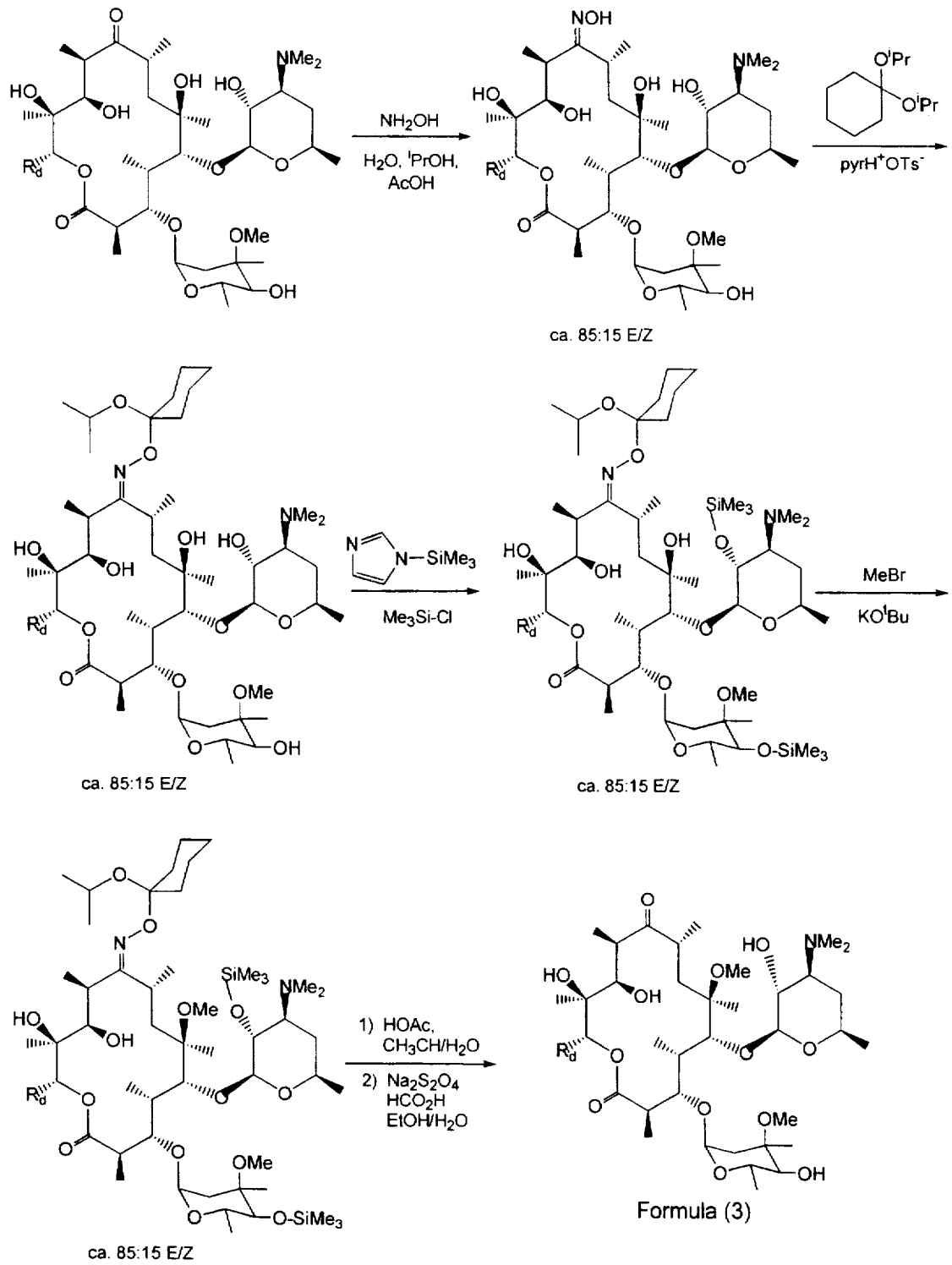
FIG. 3 shows the synthesis of compounds of formula (3) wherein $R_f$ is methyl.

The isolated products are then used as intermediates in the chemical synthesis of other intermediate compounds of the invention. For erythromycin A derivative intermediates that comprise a 6-hydroxyl, Examples 4–6 describe the process for alkylating the compounds to make the 6O-alkyl intermediates of the invention and Example 11 describes the process for allylation to make 6O-allyl intermediates which can be further derivatized as shown in Example 15 upon protection of the 2' and 4" hydroxyl groups and protection of the 9-position as shown in Example 14. The schematic for these reactions is shown in FIG. 3.

Figure 4:
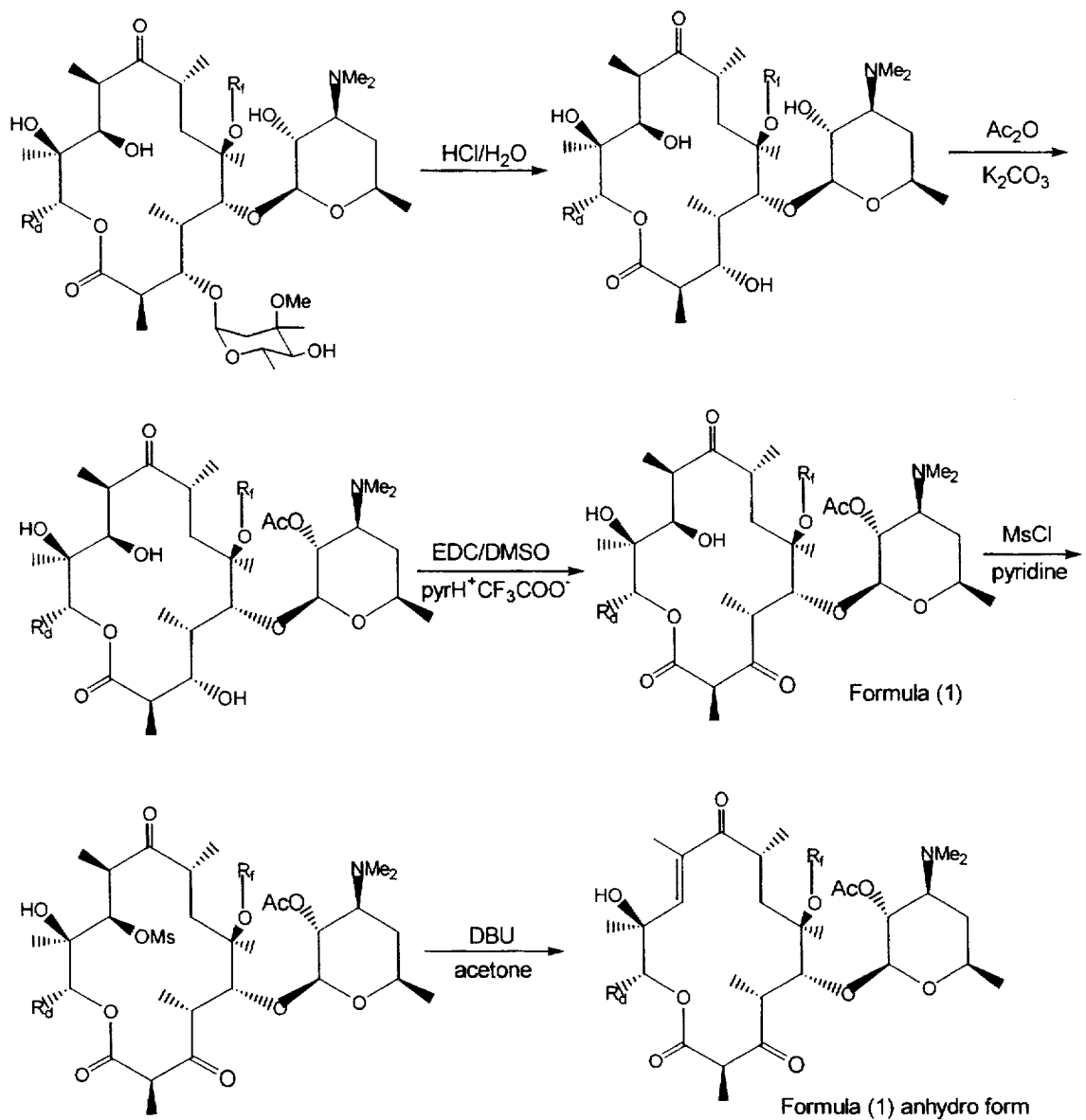
FIG. 4 shows the synthesis of compounds of formula (1) and their corresponding 10,11-anhydro forms.

Examples 7–9 describe the conversion of the above-described compounds of formula (3) to compounds of formula (1), and corresponding compounds that are the 10,11-anhydro forms. This is shown schematically in FIG. 4.

Figure 5:
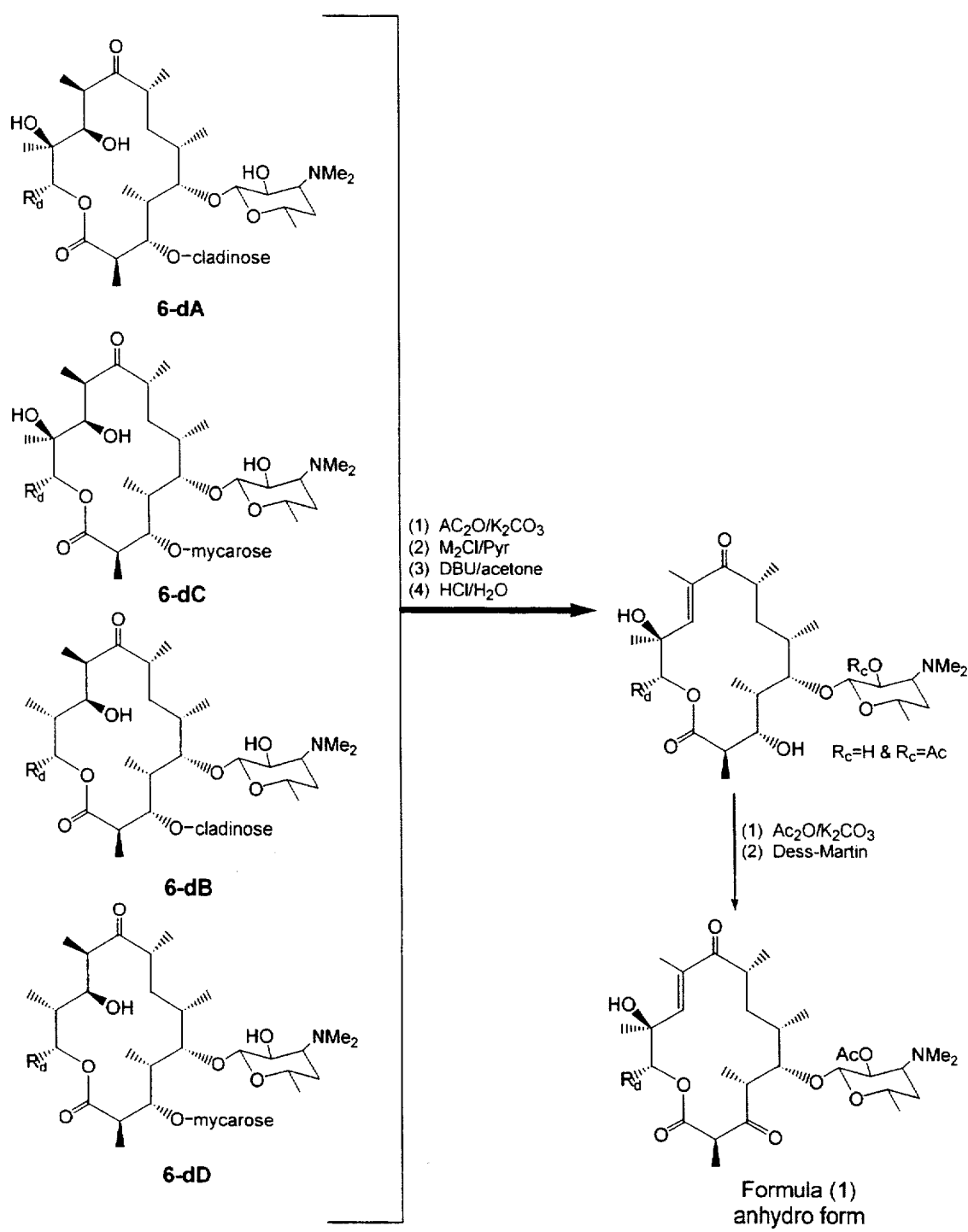
FIG. 5 shows the synthesis of compounds of formula (3) wherein $OR_f$ is replaced by H.

Example 10 also sets forth the process for making the 10,11-anhydro compounds of formula (3), but wherein $OR_f$ is replaced by H. The reaction scheme for these conversions is shown in FIG. 5.

The compounds in Example 11 can be converted to compounds of formula (1) or (2) as shown in Examples 12 and 13, respectively.

Example 16 illustrates the halogenation of the 2-position.

Figure 6:
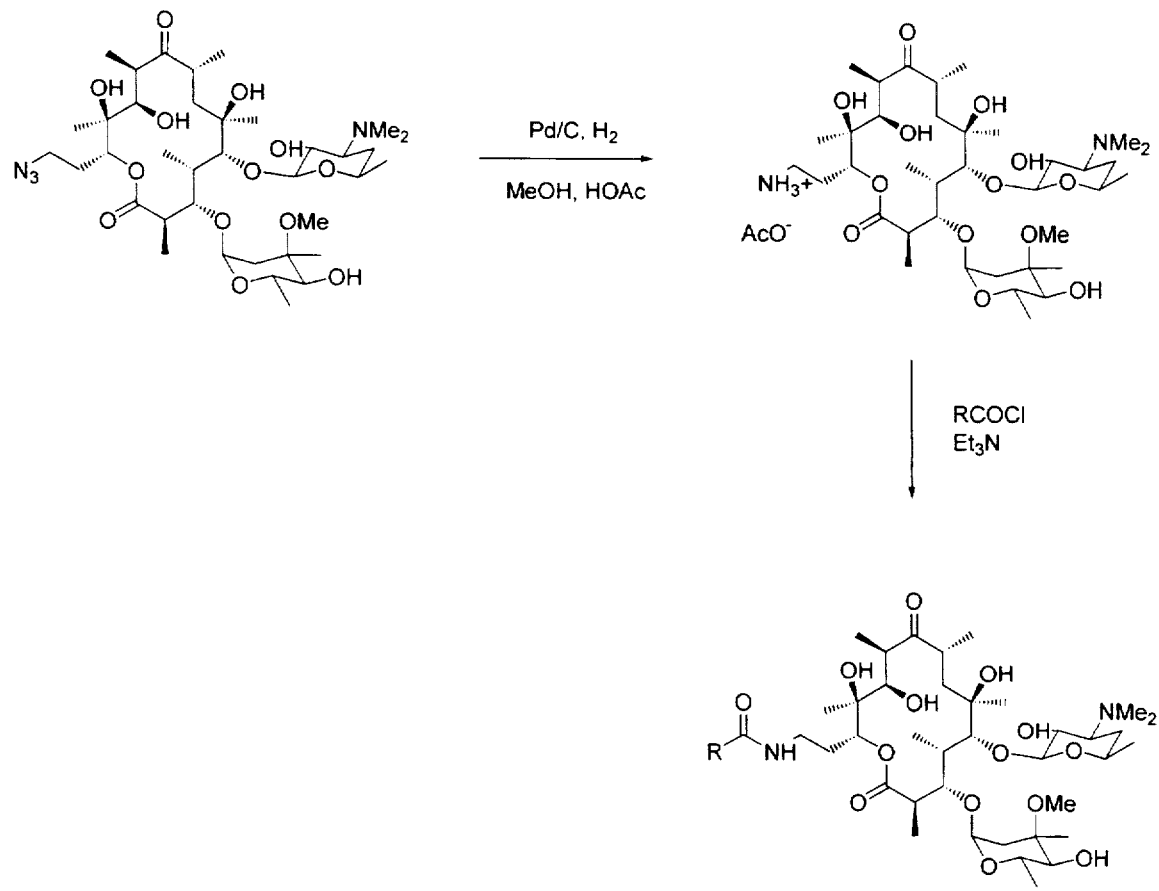
FIG. 6 illustrates the conversion of 15-azidoerythromycin A into 15-amidoerythromycins.

Example 17 illustrates the conversion of 15-azidoerythromycin A into 15-amidoerythromycins, as shown in FIG. 6.

Example 1

Preparation of Diketide Thioesters

The processes used to prepare the N-acetylcysteaminethioesters (NAcS) used to feed the recombinant Streptomyces host cells to make the 15-methyl and 14,15-dehydro-6-deoxyerythronolide B intermediate compounds are described in this Example. The synthesis protocols described below are also described in U.S. provisional patent application Ser. No. 60/117,384, filed Jan. 27, 1999 and U.S. utility patent application Ser. No. 09/492,733, filed Jan. 27, 2000, both of which are incorporated herein by reference.

Thus, (2S,3R)-2-methyl-3-hydroxyhexanoate NAcS (Preparation E), which is used to prepare the 15-methyl-6-deoxyerythronolide B intermediate, is prepared from reacting (4S)-N-[(2S,3R)-2-methyl-3-hydroxyhexanoyl]-4-benzyl-2-oxazolidinone (Preparation D) with N-acetylcysteamine (Preparation B). N-acetylcysteamine is, in turn, prepared from N,S-diacetylcysteamine (Preparation A). (4S)-N-[(2S,3R)-2-methyl-3-hydroxyhexanoyl]-4-benzyl-2-oxazolidinone (Preparation D) is prepared from (4S)-N-Propionyl-4-benzyl-2-oxazolidinone (Propionyl-NOx; Preparation C).

In similar fashion, (2S,3R)-2-methyl-3-hydroxy-4-pentenoate NAcS (Preparation G), which is used to prepare the 14,15-dehydro-6-deoxyerythronolide B intermediate, is prepared from reacting (4S)-N-[(2S,3R)-2-methyl-3-hydroxy-4-pentenoyl]-4-benzyl-2-oxazolidinone (Preparation F) with N-acetylcysteamine (Preparation B). (4S)-N-[(2S,3R)-2-methyl-3-hydroxy-4-pentenoyl]-4-benzyl-2-oxazolidinone (Preparation F) is prepared from (4S)-N-Propionyl-4-benzyl-2-oxazolidinone (Propionyl-NOx; Preparation C).

A. N,S-Diacetylcysteamine

Cysteamine hydrochloride (50.0 g) is added to a 1 L 3-neck round bottom flask fitted with a magnetic stir bar, 2 addition funnels, and a pH electrode. Water (300 mL) is added, and the stirred solution is cooled on ice. The pH is adjusted to 8.0 by addition of 8 N KOH. Acetic anhydride (125 mL) is placed in one addition funnel, and 8N KOH (350 mL) is placed in the other addition funnel. The acetic anhydride is added dropwise to the cysteamine solution, with 8 N KOH being added so as to keep the reaction pH at 8+/−1. After addition of acetic anhydride is complete, the pH was adjusted to 7.0 using 1 N HCl and the mixture is allowed to stir for 75 min. on ice.

Solid NaCl is added to saturation, and the solution is extracted 4 times using 400 ml portions of $CH_2Cl_2$. The organic extracts are combined, dried over $MgSO_4$, filtered, and concentrated under reduced pressure to yield 68.9 g (97% yield) of a pale yellow oil, which crystallizes upon standing at 4° C.

B. N-Acetylcysteamine

N,S-diacetylcysteamine (42.64 g) is placed in a 2 L round bottom flask fitted with a magnetic stirrer, and dissolved in 1400 mL of water. The flask is purged with $N_2$, and the mixture is chilled in an ice bath. Potassium hydroxide (49.42 g) is added, and the mixture is stirred for 2 hr. on ice under inert atmosphere. The pH is adjusted to 7 using 6 N HCl, and solid NaCl is added to saturation. The mixture is extracted 7 times with 500 mL portions of $CH_2Cl_2$. The organic extracts are combined, dried over $MgSO_4$, filtered, and concentrated under reduced pressure to yield 30.2 g (96% yield) of product. This material is distilled immediately prior to use, bp 138–140° C./7 mmHg.

C. (4S)-N-Propionyl-4-benzyl-2-oxazolidinone (Propionyl-NOx)

A dry, 1 L three-necked round bottomed flask equipped with a 500 mL addition funnel and a stir bar was charged with 20 g of (4S)-4-benzyl-2-oxazolidinone, capped with septa and flushed with nitrogen. Anhydrous THF (300 mL) was added by cannula and the resulting solution was cooled with a −78° C. bath of dry ice/isopropanol. The addition funnel was charged with 78 mL of n-butyllithium (1.6 M in hexane) by cannula, which was added in a slow stream to the reaction. Distilled propionyl chloride (bp 77–79° C.), 8.0 mL, was added rapidly via syringe. The reaction was allowed to stir for 30 min. in the dry ice/isopropanol bath.

The reaction was removed from the cold bath, allowed to warm to >0° C., and quenched with 50 mL of saturated aqueous $NH_4Cl$. The mixture was concentrated to a slurry on a rotary evaporator. The slurry was extracted three times with 250 mL portions of ethyl ether. The organic extracts were combined and washed with 50 mL each of saturated aqueous $NaHCO_3$ and brine, dried with $MgSO_4$, filtered, and concentrated to give a yellow oil. The material crystallized upon sitting. The crystals were triturated once with cold (−20° C.) hexanes to give 21.0 g (80% yield) of white crystalline material, m.p. 41–43° C.

APCI-MS: m/z=234 (MH+), 178, 117. 1H-NMR (360 MHz, $CDCl_3$): ∂7.2–7.4 (5Hm); 4.67 (1H,m,H4); 4.14–4.22 (2H,m,H5); 3.30 (1H,dd,J=3,13 Hz,benzylic); 2.89–3.03 (2H,m,H2'); 2.77 (1H,dd,J=9,13,benzylic); 1.20 (3H,t,J=7 Hz,H2').

D. (4S)-N-[(2S,3R)-2-methyl-3-hydroxyhexanoyl]-4-benzyl-2-oxazolidinone

A dry, 2 L three-necked round bottomed flask equipped with a 500 mL addition funnel, a low-temperature thermometer, and a stir bar was charged with 19.84 g of N-propionyl-oxazolidinone, capped with septa and flushed with nitrogen. Anhydrous dichloromethane (100 mL) was added by cannula, and the resulting solution was cooled to −65° C. in a bath of dry ice/isopropanol. The addition funnel was charged by cannula with 100 mL of dibutylboron triflate (1.0 M in dichloromethane), which was added in a slow stream to the reaction. Triethylamine (15.6 mL) was added dropwise by syringe, keeping the reaction temperature below −10° C. The reaction was then transferred to an ice bath and allowed to stir at 0° C. for 30 min. After that period, the reaction was placed back into the dry ice/isopropanol bath and allowed to cool to −65° C. Butyraldehyde (8.6 mL) was added rapidly by syringe, and the reaction was allowed to stir for 30 min.

The reaction was transferred to an ice bath and the addition funnel was charged with 100 mL of a 1 M aqueous phosphate solution, pH 7.0 (the phosphate solution is comprised of equal molar amounts of mono- and dibasic potassium phosphate). The phosphate solution was added as quickly as possible while keeping the reaction temperature below 10° C. The addition funnel was then charged with 300 mL methanol which was added as quickly as possible while keeping the reaction temperature below 10° C. Finally, the addition funnel was charged with 300 mL of 2:1 methanol:30% hydrogen peroxide. This was added dropwise to ensure that the temperature was kept below 10° C. The reaction was stirred for one hr. after completion of addition. The solvent was then removed on a rotary evaporator until a slurry remained. The slurry was extracted 4 times with 500 mL portions of ethyl ether. The combined organic extracts were washed with 250 mL each of saturated aqueous sodium bicarbonate and brine. The extract was then dried with $MgSO_4$, filtered, and concentrated to give a slightly yellow oil. The material was then chromatographed on $SiO_2$ using 2:1 hexanes:ethyl acetate (product Rf=0.4) resulting in 22.0 g (85% yield) of title compound as a colorless oil.

APCI-MS: m/z 306 (MH+); 1H-NMR (360 MHz, $CDCl_3$): ∂7.2–7.4 (5H,m, phenyl); 4.71 (1H,m,H4); 4.17–4.25 (2H,m,H5); 3.96 (1H,m,H3'); 3.77 (1H,dq,J=2.5,7 Hz, H2'); 3.26 (1H,dd,J=4,13 Hz,benzylic); 2.79 (1H,dd,J= 9,13 Hz,benzylic); 1.5–1.6 (2H,m,H4'); 1.3–1.5 (2H,m,H5'); 1.27 (3H,d,J=7 Hz,2'-Me); 0.94 (3H,t,J=7 Hz,6').

E. (2S,3R)-2-methyl-3-hydroxyhexanoate N-acetylcysteamine thioester

N-acetylcysteamine was distilled at 130° C./7 mm Hg to give a colorless liquid at room temperature. A dry, 1 L three-necked round bottomed flask equipped with a 500 mL addition funnel and a stir bar was capped with septa and flushed with nitrogen. The flask was then charged with 10.7 mL of N-acetylcysteamine by syringe and with 400 mL of anhydrous THF by cannula. The mixture was cooled with a MeOH/ice bath. Butyllithium (64 mL of 1.6 M in hexanes) was added dropwise by syringe, resulting in formation of a white precipitate. After stirring for 30 min., trimethylaluminum (51 mL of 2.0 M in hexanes) was added dropwise by syringe. The reaction became clear after addition of trimethylaluminum and was allowed to stir an additional 30 min. During this period, 20.5 g (0.068 mol) of (4S)-N-[(2S,3R)-2-methyl-3-hydroxylhexanoyl]-4-benzyl-2-oxazolidinone was put under a blanket of nitrogen and dissolved in 100 mL of anhydrous THF; this solution was then transferred in a slow stream by cannula into the reaction. The resulting reaction mixture turned a yellow-green color and was allowed to stir for 1 hr. The reaction was finished when the starting material could no longer be seen by thin-layer chromatographic analysis (ca. 1 hr.).

The reaction was treated with enough saturated oxalic acid to give a neutral reaction with pH paper (approximately 90 mL). The solvents were then removed on a rotary evaporator to give a white slurry. The slurry was extracted six times with 250 mL portions of ethyl ether. The organic extracts were combined and washed with brine, dried with $MgSO_4$, filtered, and concentrated to give a slightly yellow oil. The thioester product was purified by flash chromatography on $SiO_2$ using 1:1 hexanes:EtOAc until the elution of 4-benzyl-2-oxazolidinone. At that point, the solvent system was switched to 100% EtOAc to give pure fractions of diketide thioester. The product fractions were combined and concentrated to give 14.9 g (89% yield) of title compound. This compound is referred to as the propyl diketide thioester in Example 2.

APCI-MS: m/z 248 (MH+); 1H-NMR (360 MHz, $CDCl_3$): ∂5.8 (br s,1H); 3.94 (dt, 1H), 3.46 (m,2H), 3.03 (dt,2H), 2.71 (dq,1H), 1.97 (s,3H), 1.50 (m,2H), 1.37 (m,2H), 1.21 (d,3H), 0.94 (t,3H).

F. (4S)-N-[(2S,3R)-2-methyl-3-hydroxy-4-pentenoyl]-4-benzyl-2-oxazolidinone

A dry, 2 L three-necked round bottomed flask equipped with a 500 mL addition funnel, a low-temperature thermometer, and a stir bar was charged with 20.0 g of propionyl oxazolidinone A, capped with septa and flushed with nitrogen. Anhydrous dichloromethane (100 ml) was added and the resulting solution was cooled to −15° C. in a bath of methanol/ice. Dibutylboron triflate (100 mL of 1.0 M in dichloromethane) was added in a slow stream via the addition funnel at such a rate as to keep the reaction temperature below 3° C. Diisopropylethylamine (17.9 mL) was added dropwise by syringe, again keeping the internal temperature below 3° C. The reaction was then cooled to −65° C. using a dry ice/isopropanol bath. Acrolein was added over 5 min. by syringe. The reaction was allowed to stir for 30 min. after completion of addition. The reaction was then transferred to an ice bath and the addition funnel was charged with 120 mL (0.1 mol) of a 1 M aqueous phosphate solution, pH 7.0 (the phosphate solution is comprised of equal molar amounts of mono- and dibasic phosphate). The phosphate solution was added as quickly as possible while keeping the reaction temperature below 10° C. The addition funnel was then charged with 400 mL of methanol that were added as quickly as possible while keeping the reaction temperature below 10° C. Finally, the addition funnel was charged with 400 mL of 2:1 methanol:30% hydrogen peroxide by initial dropwise addition to keep the temperature below 10° C. The reaction was stirred for one hour. The solvent was removed using a rotary evaporator, leaving a slurry. The slurry was extracted 4 times with 500 mL portions of ethyl ether. The organic extracts were combined and washed with 250 mL each of saturated sodium bicarbonate and brine, then dried with $MgSO_4$, filtered, and concentrated to give a slightly yellow oil. Trituration with hexane induced crystallization. Recrystallization from ether by addition of hexane resulted in 13.67 g (55% yield) of product.

1 1-NMR (360 MHz, $CDCl_3$): ∂7.2–7.4 (m,5H); 5.86 (ddd,1H), 5.35 (dt,1H), 5.22 (dt,1H), 4.71 (m, 1H), 4.51 (m,1H), 4.21 (m,2H), 3.89 (dq,1H), 3.26 (dd,1H), 2.80 (dd,1H), 1.25 (d,3H).

G. (2S,3R)-2-methyl-3-hydroxy-4-pentenoate N-acetylcysteamine thioester

N-acetylcysteamine was distilled at 130° C./7 mm Hg to give a colorless liquid at room temperature. A dry,1 L three-necked round bottomed flask equipped with a 500 mL addition funnel and a stir bar was capped with septa and flushed with nitrogen. The flask was then charged with 7.5 mL of N-acetylcysteamine by syringe and with 500 mL of anhydrous THF by cannula. The reaction was then cooled with a MeOH/ice bath. Butyllithium (44 mL of 1.6 M in hexane) was added dropwise by syringe. A white precipitate formed as the n-BuLi was added. After stirring for 30 min., 35.5 mL (0.071 mol) of trimethylaluminum (2.0 M in hexane) were added drop-wise by syringe. The reaction became clear after addition of trimethylaluminum and was allowed to stir an additional 30 min. (4S)-N-[(2S,3R)-2-methyl-3-hydroxy-4-pentenoyl]-4-benzyl-2-oxazolidinone from Preparation F (13.6 g) was put under a blanket of nitrogen, dissolved in 50 mL of anhydrous THF, and this solution was then transferred in a slow stream by cannula into the reaction. The resulting reaction mixture turned a yellow-green color and was allowed to stir for 1 hr. The reaction was judged to be finished when starting material could no longer be seen by thin-layer chromatography (ca. 30 min.).

Enough saturated oxalic acid was added to give a neutral reaction with pH paper (approximately 60 mL). The solvents were then removed by rotary evaporator to give a white slurry. The slurry was extracted six times with 250 mL portions of ethyl ether. The organic extracts were combined, washed with brine, dried with $MgSO_4$, filtered, and concentrated to give a slightly yellow oil. The thioester was then purified by flash chromatography on SiO2. The column was run with 1:1 hexanes:ethyl acetate until the elution of oxazolidinone. At that point, the eluent was switched to 100% ethyl acetate to give pure fractions of product. The fractions were combined and concentrated to give 7.7 g (71% yield) of title compound product. This product is referred to as the vinyl diketide thioester in Example 2.

1H-NMR (360 MHz, $CDCl_3$): ∂5.82 (ddd,1H), 5.78 (br s,1H), 5.32 (dt,1H), 5.21 (dt,1H), 4.47 (m,1 H), 3.45 (m,2H), 3.04 (m,2H), 2.81 (dq,1H), 1.96 (s,3H), 1.22 (d,3H)

Example 2

Preparation of Erythronolides

A. 15-methyl-6-deoxyerythronolide B (Compound P, $R_a$=H, $R_d$ =propyl)

*Streptomyces coelicolor* CH999/pJRJ2 is described in U.S. patent application Ser. No. 08/896,323, filed Jul. 17, 1997, and Ser. No. 08/675,817, filed Jul. 5, 1996, each of which is incorporated herein by reference. Plasmid pJRJ2 encodes a mutated form of DEBS in which the ketosynthase domain of module 1 (KS1) has been inactivated via mutagenesis (KS1). *S. coelicolor* strains comprising this plasmid that are fed (2S, 3R)-2-methyl-3-hydroxyhexanoate-N-acetylcysteamine (Preparation E, propyl diketide) of Example 1 produce 15-methyl-6-deoxyerythronolide B.

A 1 mL vial of the CH999/pJRJ2 working cell bank is thawed and the contents of the vial are added to 50 mL of Inoculum Medium 1 in a 250 mL baffled flask. The flask is placed in an incubator/shaker maintained at 30±1° C. and 175±25 RPM for 48±10 hours. The 50 mL culture is then added to a 2.8 L baffled flask containing 500 mL of Inoculum Medium 1. This flask is incubated in an incubator/shaker at 30±1° C. and 175±25 RPM for 48±10 hours. The 500 mL culture is divided equally among ten 2.8 L baffled flasks each containing 500 mL of Inoculum Medium 1. All flasks are then incubated as described previously.

A 150 L fermenter is prepared by sterilizing 100 L of Production Medium 1 at 121° C. for 45 minutes. After incubation, all 10 flasks are combined in a 5 L sterile inoculation bottle and aseptically added to a 150 L fermenter. The fermenter is controlled at 30° C., pH 6.5 by addition of 2.5 N $H_2SO_4$ and 2.5 N NaOH, dissolved oxygen≥80% air saturation by agitation rate (500–700 RPM), air flow rate (10–50 LPM), and/or back pressure control (0.1–0.4 bar). Foam is controlled by the intermittent addition of a 50% solution of Antifoam B.

At 24±5 hours (2S, 3R)-2-methyl-3-hydroxyhexanoyl-N-acetylcysteamine (propyl diketide, Preparation E in Example 1) is added to a final concentration of 1 g/L. Propyl diketide is prepared by solubilizing in dimethyl sulfoxide at a ratio of 1:4 (diketide to DMSO) and then filter sterilized (0.2 μm, nylon filter). Production of 15-methyl-6-deoxyerythronolide B (15-methyl-6dEB) ceases on day 7 and the fermenter is harvested. The fermentation broth is centrifuged at 20,500 g in an Alpha Laval AS-26 centrifuge. The product is predominantly in the centrate; the centrifuged cell mass is discarded.

This process has also been completed in a 1000 L fermenter (700 L working volume). The inoculum process is identical to the above process except that the 150 L fermenter is charged with Inoculum Medium1 and the 1000 l fermenter is charged with Production Medium 1. The fermenter is controlled at 30° C., pH 6.5 by addition of 2.5–5 N $H_2SO4$ and 2.5–5 N NaOH, dissolved oxygen≥70% air saturation by agitation rate (140–205 RPM), air flow rate (100–200 LPM), and/or back pressure control (0.2–0.5 bar). Foam is controlled by the addition of a 50% solution of Antifoam B as needed. At 24±5 hours racemic 2-methyl-3- hydroxyhexanoyl-N-propionylcysteamine (300 grams) is added to the 1000 L fermenter. The fermenter is harvested at 4.6 days by centrifugation as described above.

Media used in this process include the following:

Inoculum Medium 1

| Component | Concentration |
|---|---|
| KNO$_3$ | 2 g/L |
| Yeast extract | 20 g/L |
| Hycase SF | 20 g/L |
| FeSO$_4$-7H$_2$O | 25 mg/L |
| NaCl (12.5% stock) | 4 mL/L |
| MgSO$_4$ (12.5% stock) | 4 mL/L |
| MnSO$_4$-H$_2$O (0.5% stock) | 1 mL/L |
| ZnSO$_4$-7H$_2$O (1.0% stock) | 1 mL/L |
| CaCl$_2$-2H$_2$O (2.0% stock) | 1 mL/L |

Sterilized by autoclaving for 60 minutes at 121° C.

Post-sterile Additions 1) 1 mL/L of 50 mg/ml Thiostrepton in 100% DMSO, sterile filtered.

2) 1 mL/L 100% Antifoam B silicon emulsion (J.T. Baker), autoclaved.

3) 40 mL of 500 g/l, glucose, sterile filtered.

Production Medium 1

| Component | g/L |
|---|---|
| Corn Starch | 45 |
| Corn steep liquor | 10 |
| Dried, inactivated brewers yeast | 10 |
| CaCO$_3$ | 1 |

Sterilized in fermenter for 45 minutes at 121° C.

Post-sterile Additions for Production Medium 1

1) 1 mL/L of 50 mg/ml Thiostrepton in 100% DMSO, sterile filtered.

2) 1 mL/L of 100% Antifoam B (J.T. Baker), autoclaved.

After centrifugation, the centrate is filtered. The filtrate (approximately 700 L) are passed through an Amicon Moduline column (20×350 cm) containing 20 L of HP20 resin (Mitsubishi). The flow rate during loading is 4 L/minute with a pressure drop below 8 psi. After loading the resin is washed with 20 L of water and then 40 L of 30% methanol. 15-methyl-6dEB is eluted using 100% methanol. Four 12 L fractions were collected with fractions 2, 3 and 4 containing all of the detectable 15-methyl-6dEB. The 15-methyl-6dEB product pool is diluted with 36.7 L of water giving 75 L of a clear solution. This solution is loaded directly onto a 5 L Amicon Vantage Column containing HP20SS resin (Mitsubishi). Column loading is carried out at 1 L/minute. The column is eluted with 20 L of 65% methanol, 20 L of 70% methanol, 20 L of 80% methanol, and finally 20 L of 100% methanol. A total of 16×5 L fractions were collected. The 80% fractions along with the last 70% fraction were combined (25 L) and evaporated to dryness. The resulting residue is dissolved in 1 L of 100% methanol, filtered, evaporated, and dried in a vacuum oven at 40° C. This process resulted in 33 g of a solid product containing 93% 15-methyl-6dEB.

B. 14,15-dehydro-6-deoxyerythronolide B (Compound P, R$_a$=H, R$_d$=—CH=CH$_2$) S. coelicolor strains comprising this plasmid that are fed (2S,3R)-2-methyl-3-hydroxy-4-pentenoate NAc Cysteamine thioester (Preparation G) of Example 1 produce 14,15-dehydro-6-deoxyerythronolide B when prepared in accordance with the process described in Preparation A above to produce 15-methyl-6-deoxyerythronolide B.

C. 14-nor-6-deoxyerythronolide B (Compound P, R$_a$=H, R$_d$=methyl)

Similarly, 14-nor-6-deoxyerythronolide B is produced using S. coelicolor CH999/pCK7 host, without using a diketide thioester, when prepared in accordance with the process described in Example 2A.

Example 3

Preparation of Erythromycins

The 6-dEB derivative compounds produced in Example 2, Preparations A–C are converted to erythromycin derivatives using a recombinant strain of Saccharopolyspora erythraea. For production of erythromycins having both the 6 and 12 hydroxyl groups, the S. erythraea strain used was K40–67 or K39–14V. This strain was created by transforming an S. erythraea strain capable of producing high levels of erythromycin A with a pWHM3-derived plasmid comprising a mutated eryA 1 sequence encoding an inactivated KS 1 domain. By homologous recombination, the resulting transformants were rendered incapable of producing 6-deoxyerythronolide B. Thus the dEB analog fed is not subject to competition for hydroxylation at the 6-position. For production of erythromycin derivatives having only the 12-hydroxyl group, the S. erythraea strain used was K39-07. This strain was constructed from strain K40-67 by disruption of the eryF hydroxylase gene; this destroys ability to hydroxylate the analog at the 6-position. Both strains were fermented under substantially similar conditions, as described below.

15-methyl-erythromycin A 15-methyl-erythromycin A is produced according to the following protocol: A 1 mL vial of the K39-14V working cell bank is thawed and the contents of the vial are added to 50 mL of Inoculum Medium 2 in a 250 mL baffled flask. The flask is placed in an incubator/shaker maintained at 34±1° C. and 175±25 RPM for 48±10 hours. The 50 mL culture is then added to a 2.8 L baffled flask containing 500 mL of Inoculum Medium 2. The flask is incubated in an incubator/shaker at 34±1° C. and 175±25 RPM for 48±10 hours. The 500 mL culture is divided equally among ten 2.8 L baffled flasks each containing 500 mL of Inoculum Medium 2. All flasks are then incubated as described previously.

A 150 L fermenter is prepared by sterilizing 100 L of Production Medium 2 at 121° C. for 45 minutes. After incubation, all 10 flasks are combined in a 5 L sterile inoculation bottle and aseptically added to a 150 L fermenter. The fermenter is controlled at 34° C., pH 7.0 by addition of 2.5 N H$_2$SO$_4$ and 2.5 N NaOH, dissolved oxygen≧80% air saturation by agitation rate (500–700 RPM), air flow rate (15–50 LPM), and/or back pressure control (0.1–0.4 bar). Foam is controlled by the addition of a 50% solution of Antifoam B.

At 24±5 hours a 58–60 mL/hour 15% dextrin (w/v) feed is initiated. The dextrin solution is continuously mixed during the feed period. At 24±5 hours 25 grams of 15-methyl-6dEB (Preparation A in Example 2) are added to the fermenter. The 15-methyl-6dEB is prepared by solubilizing 25 grams of 15-methyl-6dEB in 400–600 mL of 100% ethanol and filtering (0.2 μm, nylon filter). Conversion of 15-methyl-6dEB to 15-methyl-erythromycin A ceases after 60±10 hours and the fermenter is harvested. The fermentation broth is centrifuged at 20,500 g in an Alpha Laval AS-26 centrifuge. The product is predominantly in the centrate; the centrifuged cell mass is discarded.

Media used in this process include the following:

Inoculum Medium 2

| Component | g/L |
|---|---|
| Corn Starch | 16.0 |
| Corn dextrin | 10.0 |
| Soy Meal Flour | 15.0 |
| $CaCO_3$ | 4.0 |
| Corn steep liquor | 5.0 |
| Soy Bean Oil | 6.0 |
| NaCl | 2.5 |
| $(NH_4)_2SO_4$ | 1.0 |

Sterilized by autoclaving for 60 minutes at 121° C.
Post-sterile addition
1 mL/L 100% Antifoam B (J. T. Baker), autoclaved.

Production Medium 2

| Component | g/L |
|---|---|
| Corn Starch | 17.5 |
| Corn Dextrin (Type 3) | 16.0 |
| Soy Meal Flour | 16.5 |
| $CaCO_3$ | 4.0 |
| Corn steep liquor | 6.0 |
| Soy Bean Oil | 3.0 |
| NaCl | 3.5 |
| $(NH_4)_2SO_4$ | 1.0 |

Sterilized in fermenter for 45 minutes at 121° C.

Centrifuged fermentation broth (127 L) containing 34 g of the target molecule is passed through 18.3 L of HP20 sorbent packed into an Amicon P350 Moduline 2 chromatography column. At 4 L/min loading, backpressure is found to be less than 5 psi. Following loading, the resin is washed with 20 L deionized water and then 40 L of 30% methanol. 15-Methyl-Erythromycin A is eluted using 54 L of 100% methanol. The product pool is evaporated using a Buchi rotary evaporator (R-152). The solids were dissolved in a minimal amount of 100% methanol, filtered and the filtrate evaporated to dryness. This resulted in 123 g of material containing 30% 15-Methyl-Erythromycin A by weight. 80 grams of the 30% material is extracted twice with 1 L of 40° C. acetone. The acetone extract is filtered, and the filtrate is dried on the inside surface of a 20 L rotary evaporation flask. The solids were extracted with 9:1 hexane to acetone three times at 40° C. The organic extracts were pooled and evaporated to dryness giving 32 g of solids enriched (68%) in 15-Methyl-Erythromycin A. The product pool from the acetone/hexane extraction is dissolved in 1 L of methanol to which an equal amount of water is added. The methanol solution is loaded onto a HP20SS chromatography column (Kontes) previously washed and equilibrated with 50% methanol. Column dimensions were 4.8×115 cm. Column loading with respect to 15-Methyl-Erythromycin A is 11 g/L. The column is washed with 50% (0.8 L) and 60% (8 L) methanol in water. Elution of the target molecule is carried out using 70% (8L), 80% (16 L) and 85% (8 L) methanol in water. 1 L fractions were collected. Fractions 11–29 were combined, evaporated and dried in a vacuum oven giving 23 g of product with 93% purity.

This material served as starting material for the chemical derivatization procedures described in the following examples. The following compounds are also produced by this methodology: 14-norerythromycin A ($R_a$=Me); 14,15-dehydro-erythromycin A ($R_a$=—CH=CH$_2$); 14-nor-6-deoxy-erythromycin A; 14,15-dehydro-6-deoxy-erythromycin A; and 15-methyl-6-deoxy-erythromycin A. When used to make 3-descladinose-3-oxo-derivatives, the erythromycin A derivatives were not separated from the erythromycin C derivatives; instead, mixtures of the erythromycin A and erythromycin C compounds were used as starting materials for chemical derivatization.

These products were extracted and purified as follows:

In general, fermentation broths are brought to pH 8.0 by addition of NaOH and ethanol is added (0.1 L/L broth). The broth is clarified by centrifugation and loaded onto an XAD-16 resin (Rohm and Haas) column (1 kg XAD/1 g erythromycin analogs) at a flow rate of 2–4 mL/cm$^2$-min. The loaded resin is washed with 2 column volumes of 20% (v/v) ethanol in water and the erythromycin analogs are eluted from the resin with acetone and collected in ½ column volume fractions. The fractions containing erythromycin analogs are identified by thin-layer chromatography (ethyl acetate:hexanes 1:1) and HPLC/MS.

The acetone fractions containing erythromycin analogs are pooled and the volatiles are removed under reduced pressure. The resulting aqueous mixture is extracted with ethyl acetate. The ethyl acetate extract is washed with saturated $NaH_2CO_3$ and brine solutions, dried over sodium or magnesium sulfate, filtered, and concentrated to dryness under reduced pressure. Crude material is dissolved in dichloromethane and loaded onto a pad of silica gel and washed with dichloromethane:methanol (96:4 v/v) until the eluent is no longer yellow. The desired material is with dichloromethane:methanol:triethylamine (94:4:2 v/v) and collected in fractions. Fractions containing erythromycin are identified by thin-layer chromatography, collected and concentrated under reduced pressure. This material is recrystallized from dichloromethane/hexanes.

This general procedure is illustrated as follows:
(i) 14-norerythromycins 1 liter of ethanol was added to each of 10 liters of fermentation broth. The broth was centrifuged and the supernatant was passed through 0.6 liters of XAD (column dimensions 17 cm×6.5 cm) at a flow rate of 100 mL/min. After loading, the column was washed with 1.5 liters of 20% (v/v) ethanol in water. The desired material was then eluted with acetone. The fractions containing this material were concentrated under reduced pressure until the volatiles were removed and the aqueous remainder was extracted with ethyl acetate. The ethyl acetate layers were washed with saturated sodium bicarbonate solution, brine, dried with magnesium sulfate and concentrated under reduced pressure to give the crude extract.

Crude material (0.6 g) was dissolved in dichloromethane and gravity filtered through a 3 cm pad of silica gel in a 6 cm diameter fritted funnel. The material was eluted with 400 mL of dichloromethane followed by 400 mL dichloromethane:methanol:triethylamine (90:10:2 v/v) and collected in 40 mL fractions. Fractions containing erythromycin were identified by thin-layer chromatography (ether:methanol:$NH_4OH$ 90:8:2 v/v, Rf–0.35 and dichloromethane:methanol 95:5 v/v, Rf–0) and concentrated under reduced pressure. This material was recrystallized from dichloromethane/hexanes.

(ii) 15-methyl-erythromycins 8 liters of ethanol was added to approximately 80 liters of fermentation broth. The broth was centrifuged and the supernatant was passed through 2.5 liters of XAD at a flow rate of 230 mL/min. After loading the column was washed with 1 liter of water and 5 liters of 20% (v/v) ethanol in water. The desired material was then eluted with acetone. The fractions containing this material were concentrated under reduced pressure until the volatiles were removed and the aqueous remainder was extracted with ethyl acetate. The ethyl acetate layers were washed with saturated sodium bicarbonate solution, brine, dried with magnesium sulfate and concentrated under reduced pressure to give the crude extract Crude material (8.3 g) was dissolved in dichloromethane and gravity filtered through a 3 cm pad of silica gel in a 9 cm diameter fritted funnel. The material was eluted with 200 mL of dichloromethane followed by 600 mL of dichloromethane: methanol (96:4 v/v) followed by 900 mL, dichloromethane:methanol:triethylamine (89:9:2 v/v) and collected in 40 mL fractions. Fractions containing erythromycin were identified by thin-layer chromatography (ether:methanol:NH$_4$OH 90:8:2 v/v, R$_f$~0.4 and dichloromethane:methanol 95:5, R$_f$~0.05) and concentrated under reduced pressure. This material was re-subjected to the above procedure before it was suitable for recrystallization.

(iii) 14-nor-6-deoxy-erythromycins 1 liter of ethanol was added to each of 2 10 liter fermenting. The broths were centrifuged and the supernatants were combined for a total of approximately 22 liters. The combined broths were then passed through 1 liter of XAD (column dimensions 23.5 cm×6.5 cm (i.d.) at a flow rate of 170 mL/min. After loading the column was washed with 2 liters of 20% (v/v) ethanol in water. The desired material was then eluted with acetone. The fractions containing this material were concentrated under reduced pressure until the volatiles were removed and the aqueous remainder was extracted with ethyl acetate. The ethyl acetate layers were washed with saturated sodium bicarbonate solution, brine, dried with magnesium sulfate and concentrated under reduced pressure to give the crude extract.

(iv) 15-methyl-6-deoxy-erythromycins 1 liter of ethanol was added to each of 3 fermentors containing 10 liters of broth. The broths were centrifuged and the supernatant was passed over 1.25 liters of XAD (column dimensions 40 cm×6.5 cm) at a flow rate of 130 mL/min. The column was then washed with 3 liters of 20% (v/v) ethanol in water. The desired material was then eluted with acetone. The fractions containing this material were concentrated under reduced pressure until the volatiles were removed and the aqueous remainder was extracted with ethyl acetate. The ethyl acetate layers were washed with saturated sodium bicarbonate solution, brine, dried with magnesium sulfate and concentrated under reduced pressure to give the crude extract.

Crude material (2.8 g) was dissolved in dichloromethane and gravity filtered through a 3 cm pad of silica gel in a 6 cm diameter fritted funnel. The material was eluted with 400 mL of dichloromethane:methanol (96:4 v/v) followed by 400 mL dichloromethane:methanol:triethylamine (89:9:2 v/v) and collected in 40 mL fractions. Fractions containing erythromycin were identified by thin-layer chromatography (ether:methanol:NH$_4$OH 90:8:2 v/v and dichloromethane:methanol 95:5) and concentrated under reduced pressure. This material required further purification by silica gel chromatography.

Example 4

Synthesis of 6-O-methyl-14-norerythromycin A, i.e., Formula (3) where

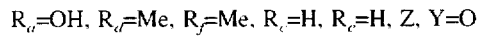

R$_a$=OH, R$_d$=Me, R$_f$=Me, R$_c$=H, R$_e$=H, Z, Y=O

A. 14-Norerythromycin A 9-Oxime

A solution of 14-norerythromycin A (0.621 g, 80% pure), hydroxylamine (0.5 ml of 50% aqueous solution) and acetic acid (0.2 ml) in isopropanol (2 ml) was kept at 50° C. for 22 hours. It was extracted with chloroform/ethanol (3/2), washed with sodium bicarbonate, brine, and dried over MgSO$_4$. Filtration and evaporation in vacuo yielded a crude product (0.65 g) as a white solid which was used directly for next transformation.

B. 14-Norerythromycin A-9-[(O-(1-isopropoxycyclohexyl)]oxime

To a solution of above crude 14-norerythromycin A 9-oxime (0.65 g) and 1,1-diisopropoxy-cyclohexanone (0.95 ml) in methylene chloride (2 ml) was added pyridinium p-toluenesulfonate (PPTS) (0.333 g) in methylene chloride (2 ml). After stirring overnight, the mixture was extracted (chloroform/ethanol 3:2), washed (NaHCO$_3$—H$_2$O, brine), and dried (MgSO$_4$). After filtration and evaporation in vacuo, the crude product was repeatedly driven with toluene and isopropanol to yield 0.74 g of product, which was used directly for next reaction.

C. 2',4"-bis-O-trimethylsilyl-14-norerythromycin A-9-[O-(1-isopropoxycyclohexyl)]oxime To a solution of 14-norerythromycin A 9-[O-(1-isopropoxycyclohexyl)]oxime (0.74 g) in methylene chloride (6 ml) was added a solution of trimethylsilyl imidazole (0.33 ml) and trimethylsilyl chloride (0.18 ml) in methylene chloride (2 ml) at 0° C. After 5 minute stirring, ethyl acetate was added, washed (NaHCO$_3$—H$_2$O, brine), and dried (MgSO$_4$). Flash chromatography on silica gel (10:1 hexanes:acetone, 1% triethylamine) afforded pure product as a white solid (0.50 g). Mass spectrometry reveals [M+H$^+$]= 1020.

D. 6-O-Methyl-2',4"-bis-O-trimethylsilyl-14-norerythromycin A-9-[O-(1-isopropoxycyclohexyl)] oxime A solution of 2',4"-bis-O-trimethylsilyl-14-norerythromycin A 9-[O-(1-isopropoxycyclohexyl)]oxime (0.3 g, 0.29 mmol) in 1:1 methylsulfoxide/tetrahydrofuran (DMSO/THF) (1.4 ml) was treated with 0.3 ml of a 2 M solution of methyl bromide in ether and cooled to 10° C. A mixture of 1 M solution of potassium tert-butoxide in THF (0.6 ml) and DMSO (0.6 ml) was added over 6 hours using a syringe pump. The reaction was then diluted with ethyl acetate, washed with saturated NaHCO$_3$, brine, and dried over MgSO$_4$. Filtration and evaporation in vacuo yielded a crude product (0.29 g) as a white solid. Mass spectrometry reveals [M+H$^+$]=1034.

E. 6-O-Methyl-14-norerythromycin A 9-oxime

A mixture of 6-O-methyl-2',4"-bis-O-trimethylsilyl-14-norerythromycin A 9-[O-(1-isopropoxycyclohexyl)]oxime (0.29 g), acetic acid (3.6 ml), acetonitrile (6 ml) and water (3 ml) was stirred at ambient temperature for 4.5 hours. The mixture was driven to dryness using toluene to give a crude product as white solid (0.24 g), which was used directly for next step without further purification.

F. 6-O-Methyl-14-norerythromycin A

A mixture of 6-O-methyl-14-norerythromycin A 9-oxime (0.24 g), sodium hydrosulfite (0.45 g, 85% pure), water (3 ml), ethanol (3 ml) and formic acid (0.07 ml) was kept at 85° C. for 8 hours. The reaction was brought to pH 8 with 1 N NaOH and extracted with ethyl acetate. The organic extract was washed with brine, dried over MgSO$_4$, filtered, and concentrated to yield a crude product as a white solid (0.2 g). Mass spectrometry reveals [M+H$^+$]=735.

Example 5

Synthesis of 6-O-methyl-14,15-dehydroerythromycin A, i.e., Formula (3) where
R$_a$=OH, R$_d$=—CH=CH$_2$, R$_c$=Me A. 14,15-dehydroerythromycin A 9-oxime A suspension of 14,15-dehydroerythromycin A (1.984 g, 47% purity, 1.2 mmol) in 6 mL of 2-propanol was treated with 1.97 mL of 50% aqueous hydroxylamine and stirred until dissolved. Acetic acid (0.62 mL) was added and the mixture was stirred for 25 hours at 50° C. Upon cooling to ambient temperature, saturated NaHCO$_3$ was added and the mixture was concentrated en vacuo to remove isopropanol. The resulting aqueous mixture was extracted three times with 250-mL portions of CHCl$_3$. The organic extracts were combined, washed with saturated NaHCO$_3$, water, and brine, then dried over MgSO$_4$, filtered, and concentrated to yield 0.92 g of product.

B. 14,15-dehydroerythromycin A 9-[O-(1-isopropoxycyclohexyl)]oxime

The oxime from (A) (0.92 g) was dissolved in 6.2 mL of CH$_2$Cl$_2$ and treated with 1,1-diisopropoxycyclohexane (1.23 g) and pyridinium p-toluenesulfonate (0.464 gm) for 15 hours at ambient temperature. The mixture was diluted with 160 mL of CH$_2$Cl$_2$, then washed sequentially with saturated NaHCO$_3$, water, and brine. The organic phase was dried with MgSO$_4$, filtered, and evaporated to yield a brown syrup. Chromatography on silica gel (gradient from toluene to 1:1 toluene/acetone+1% Et$_3$N) yielded 0.998 g of product.

C. 2',4"-bis(O-trimethylsilyl)-14,15-dehydroerythromycin A 9-[O-(1-isopropoxycyclohexyl)]oxime A solution of 14,15-dehydroerythromycin A 9-[O-(1-isopropoxycyclohexyl)]oxime (998 mg, 9.96) in 11.25 mL of CH$_2$Cl$_2$ was cooled on ice under inert atmosphere and treated with a solution of chlorotrimethylsilane (0.24 mL) and 1-trimethylsilylimidazole (0.44 mL). After 30 minutes, the reaction was diluted with 250 mL of ethyl acetate and washed sequentially with saturated NaHCO$_3$, water, and brine. The organic phase was dried with MgSO$_4$, filtered, and evaporated to yield 1.002 g of product.

D. 2',4"-bis(O-trimethylsilyl)-6-O-methyl-14,15-dehydroerythromycin A 9-[O-(1-isopropoxycyclohexyl)]oxime A solution of 2',4"-bis-O-trimethylsilyl-14,15-dehydroerythromycin A 9-[O-(1-isopropoxycyclohexyl)] oxime (1.00 g, 20.7 mmol) in 9.69 ml, of 1:1 tetrahydrofuran/methylsulfoxide was cooled to 10° C. and treated with 0.97 mL of 2.0 M methyl bromide in ether under inert atmosphere. A mixture of methylsulfoxide (1.94 mL) and 1.0 M potassium tert-butoxide in tetrahydrofuran (1.94 mL) was added slowly. The reaction was monitored by thin-layer chromatography (silica gel, 10:1 toluene/acetone), and was judged complete after addition of 1.6 molar equivalents of base. The reaction was diluted with 200 mL of ethyl acetate and 70 mL of saturated NaHCO$_3$. The mixture was transferred to a separatory funnel, diluted with 850 mL of ethyl acetate and 280 mL of saturated NaHCO$_3$, then washed sequentially with water and brine. The organic phase was dried with MgSO$_4$, filtered through Celite, and evaporated to yield 21.2 g of crude 6-O-methyl-2',4"-bis-O-trimethylsilyl-14,15-dehydroerythromycin A 9-[O-(1-isopropoxycyclohexyl)]oxime. This was carried on without further purification.

E. 6-O-methyl-14,15-dehydroerythromycin A 9-oxime

A solution of 6-O-methyl-2',4"-bis-O-trimethylsilyl-14, 15-dehydroerythromycin A 9-[O-(1-isopropoxycyclohexyl)] oxime (1.0 g) in 9.8 mL of 2:1 acetonitrile/water was treated with 5.3 mL of acetic acid, and stirred for 8 hours at ambient temperature. The mixture was concentrated en vacuo, then repeatedly concentrated after addition of toluene to yield 0.797 g of crude 6-O-methyl-14,15-dehydroerythromycin A 9-oxime.

F. 6-O-methyl-14,15-dehydroerythromycin A

A solution of 6-O-methyl-14,15-dehydroerythromycin A 9-oxime(0.797 g) and sodium hydrosulfite (85%, 1.02 g) in 7.5 mL of 1:1 ethanol/water was placed under inert atmosphere. Formic acid (0.186 mL) was added dropwise, and the mixture was stirred at 80° C. for 3 hours. After cooling to ambient temperature, the reaction was adjusted to pH 10 with 6 N NaOH and extracted three times with 150-mL portions of ethyl acetate. The organic extracts were combined and washed sequentially with saturated NaHCO$_3$, water, and brine. The organic phase was dried with MgSO$_4$, filtered, and evaporated to yield 0.68 g of 6-O-methyl-14, 15-dehydroerythromycin A suitable for further conversion.

Example 6

Synthesis of 6-O-methyl-15-methylerythromycin A, i.e., Formula (3) where R$_a$=OH, R$_d$=propyl, R$_f$=Me

A. 15-Methylerythromycin A 9-Oxime

A suspension of 15-methylerythromycin A (20.0 g, 85% purity, 22.6 mmol) in 40 mL of 2-propanol was treated with 20.5 mL of 50% aqueous hydroxylamine and stirred until dissolved. Acetic acid (6.41 mL) was added and the mixture was stirred for 15 hours at 50° C. Upon cooling to ambient temperature, saturated NaHCO$_3$ was added and the mixture was concentrated en vacuo to remove isopropanol. The resulting aqueous mixture was extracted three times with 250-mL portions of CHCl$_3$. The organic extracts were combined, washed with saturated NaHCO$_3$, water, and brine, then dried over MgSO$_4$, filtered, and concentrated to yield 20.5 g of crude product. Analysis by LC/MS revealed a 94:6 mixture of E and Z oximes, [M+H]$^+$=764.

B. 15-Methylerythromycin A 9-[O-(1-isopropoxycyclohexyl)]oxime

The crude oxime from above (20.5 g) was dissolved in 55 mL of CH$_2$Cl$_2$ and treated with 1,1-diisopropoxycyclohexane (27.3 mL) and pyridinium p-toluenesulfonate (9.8 gm) for 15 hours at ambient temperature. The mixture was diluted with 160 ml of CH$_2$Cl$_2$, then washed sequentially with saturated NaHCO$_3$, water, and brine. The organic phase was dried with MgSO$_4$, filtered, and evaporated to yield a brown syrup. Chromatography on silica gel (gradient from 2:1 to 3:2 hexanes/acetone+1% Et$_3$N) yielded 18.0 g of product.

C. 2',4"-bis-O-trimethylsilyl-15-methylerythromycin A 9-[O-(1-isopropoxycyclohexyl)]oxime A solution of 15-Methylerythromycin A 9-[O-(1-isopropoxycyclohexyl)]oxime (9.00 g, 9.96 mmol) in 25 mL of CH$_2$Cl$_2$ was cooled on ice under inert atmosphere and treated with a solution of chlorotrimethylsilane (1.89 mL) and 1-trimethylsilylimidazole (3.65 mL) in 8 mL of CH$_2$Cl$_2$. After 30 minutes, the reaction was diluted with 250 mL of ethyl acetate and washed sequentially with saturated NaHCO$_3$, water, and brine. The organic phase was dried with MgSO$_4$, filtered, and evaporated. The crude product was purified by silica gel chromatography (gradient from hexanes to 10:1 hexanes/acetone+1% Et$_3$N), yielding 7.8 g of product.

D. 6-O-Methyl-2',4"-bis-O-trimethylsilyl-15-methylerythromycin A 9-[O-(1-isopropoxycyclohexyl)]oxime A solution of 2',4"-bis-O-trimethylsilyl-15-methylerythromycin A 9-[O-(1-isopropoxycyclohexyl)]

oxime (21.7 g, 20.7 mmol) in 41.4 mL of tetrahydrofuran was cooled to 10° C. and treated with 41.4 mL of methylsulfoxide and 20.7 mL of 2.0 M methyl bromide in ether under inert atmosphere. A mixture of methylsulfoxide (41.4 mL) and 1.0 M potassium tert-butoxide in tetrahydrofuran (41.4 mL) was added at a rate of ca. 20 mL per hour. The reaction was monitored by thin-layer chromatography (silica gel, 10:1 toluene/acetone), and was judged complete after addition of 1.6 molar equivalents of base. The reaction was diluted with 200 mL of ethyl acetate and 70 mL of saturated NaHCO$_3$. The mixture was transferred to a separatory funnel, diluted with 850 mL of ethyl acetate and 280 mL of saturated NaHCO$_3$, then washed sequentially with water and brine. The organic phase was dried with MgSO$_4$, filtered through Celite, and evaporated to yield 21.2 g of crude 6-O-methyl-2',4"-bis-O-trimethylsilyl-15-methylerythromycin A 9-[O-(1-isopropoxycyclohexyl)] oxime. This was carried on without further purification.

E. 6-O-Methyl-15-methylerythromycin A 9-oxime

A solution of 6-O- methyl-2',4"-bis-O-trimethylsilyl-15-methylerythromycin A 9-[O-(1-isopropoxycyclohexyl)] oxime (21.2 g) in 110 mL of acetonitrile was treated with 55 mL of water and 67 mL of acetic acid, and stirred for 8 hours at ambient temperature. The mixture was concentrated en vacuo, then repeatedly concentrated after addition of toluene to yield 19.7 g of 6-O-methyl-15-methylerythromycin A 9-oxime.

F. 6-O-Methyl-15-methylerythromycin A

A solution of 6-O-methyl-15-methylerythromycin A 9-oxime (19.7 g) and sodium hydrosulfite (85%, 23.1 g) in 280 mL of 1:1 ethanol/water was placed wider inert atmosphere. Formic acid (3.75 mL) was added dropwise, and the mixture was stirred at 80° C. for 4.5 hours. After cooling to ambient temperature, the reaction was treated with saturated NaHCO$_3$ and extracted three times with 400-mL portions of ethyl acetate. The organic extracts were combined and washed sequentially with saturated NaHCO$_3$, water, and brine. The organic phase was dried with MgSO$_4$, filtered, and evaporated to yield 15.1 g of 6-O-methyl-15-methylerythromycin A suitable for further conversion.

Example 7

Synthesis of 5-O-(2'-Acetyldesosaminyl)-10,11-anhydro-3-deoxy-3-oxo-6-O-methyl-14-norerythronolide A (Anhydro form of Formula (1), R$_a$=OH, R$_d$=Me, R$_f$=Me, R$_c$=Ac, R$_b$=H)

A. 5-O-Desosaminyl-6-O-methyl-14-norerythronolide A

A mixture of 6-O-methyl-14-norerythromycin A (77 mg), 0.073 ml of 12 N HCl and water (2 ml) was stirred at ambient temperature for 3 hours. The mixture was brought to pH 8 with 8 N KOH, and extracted with ethyl acetate. The organic extract was washed with brine, dried with MgSO$_4$, filtered, and evaporated. The residue was chromatographed on silica gel (3:1/hexanes:acetone, 1% triethylamine) to give pure product as a white solid (42 mg). Mass spectrometry reveals [M+H$^+$]=576.

B. 5O-(2'-Acetyldesosaminyl)-6-O-methyl-14-norerythronolide A

A mixture of 5-O-desosaminyl-6-O-methyl-14-norerythronolide A (73 mg), potassium carbonate(20 mg), acetic anhydride (14 μl) and acetone (1 ml) was stirred at ambient temperature for 18 hours. Ethyl acetate was added, washed with water and brine, dried over MgSO$_4$, filtered, and evaporated. The residue was chromatographed on silica gel (3:1/hexanes:acetone, 1% triethylamine) to yield the pure product (71 mg) as a white solid. Mass spectrometry reveals [M+H$^+$]=618.

C. 5-O-(2'-Acetyldesosaminyl)-3-deoxy-3-oxo-6-O-methyl-14-norerythronolide A (Formula (1), R$_a$= OH, R$_d$=Me, R$_f$=Me, R$_b$=H, R$_c$=Ac)

A solution of 5-O-(2'-acetyldesosaminyl)-6-O-methyl-14-norerythronolide A (99 mg) and 1-(3-dimethylaminopropyl)-3-ethylcarbodiimide (EDC) hydrochloride (206 mg) in dichloromethane (2 ml) was treated with DMSO (0.21 ml) and cooled to 5° C. A solution of pyridinium trifluoroacetate (208 mg) in dichloromethane (2 ml) was added via a syringe pump in 4 hours. Ethyl acetate was then added, washed with saturated NaHCO$_3$, water, brine, and dried over MgSO$_4$, filtered, and evaporated. The residue was chromatographed on silica gel (3:1/hexanes:acetone, 1% triethylamine) to yield the pure product (94 mg) as a white solid. Mass spectrometry reveals [M+H$^+$]=616.

D. 5-O-(2'-Acetyldesosaminyl)-3-deoxy-3-oxo-11-O-methanesulfonyl-6-O-methyl-14-norerythronolide A To a solution of 5-O-(2'-acetyldesosaminyl)-3-deoxy-3-oxo-6-O-methyl-14-norerythronolide A (93 mg) in dry pyridine (1 ml) was added methanesulfonyl chloride (0.057 ml) at 5° C. After 3 hours at 5° C., the reaction was warmed to ambient temperature and kept for an additional 15 hours. The mixture was diluted with ethyl acetate, washed with saturated NaHCO$_3$(2×), water (3×), brine, and dried over MgSO$_4$, filtered, and evaporated. The residue was chromatographed on silica gel (2:1/hexanes:acetone, 1% triethylamine) to yield the pure product (72 mg) as a white solid. Mass spectrometry reveals [M+H$^+$]=695.

E. 5-O-(2'-Acetyldesosaminyl)-10,11-anhydro-3-deoxy-3-oxo-6-O-methyl-14-norerythronolide A A solution of 5-O-(2'-acetyldesosaminyl)-3-deoxy-3-oxo-11-O-methanesulfonyl-6-O-methyl-14-norerythronolide A (73 mg) in acetone (1 ml) was treated with diazabicycloundecene (32 μl) at ambient temperature for 18 hours. The mixture was diluted with ethyl acetate, washed with saturated NaHCO$_3$, water, brine, and dried over MgSO$_4$, filtered, and evaporated. The residue was chromatographed on silica gel (2:1/hexanes:acetone, 1% triethylamine) to yield the pure product (50 mg) as a white solid. Mass spectrometry reveals [M+H$^+$]=598.

$^{13}$C-NMR (CDCl$_3$, 100 MHz): δ207.02, 204.50, 169.63, 168.72, 142.52, 139.40, 101.87, 80.61, 80.02, 77.14, 72.66, 71.48, 69.09, 63.56, 51.35, 50.56, 47.12, 40.61, 39.73, 37.36, 30.36, 21.32, 21.06, 20.96, 20.67, 18.45, 14.34, 13.89, 13.55, 13.45.

Example 8

Synthesis of 2'-O-Benzoyl-6-O-methyl-3-descladinosyl-3-oxo-10,11-anhydro-14,15-dehydroerythromycin A (Anhydro form of Formula (1), R$_a$=OH, R$_d$=—CH=CH$_2$, R$_f$=Me, R$_b$=H, R$_c$= Benzoyl)

A. 2'-O-Benzoyl-6-O-methyl-14,15-dehydroerythromycin A

A solution of 6-O-methyl-14,15-dehydroerythromycin A (668 mg), benzoic anhydride (385 mg), and triethylamine (0.25 mL) in 3.6 mL of $CH_2Cl_2$ was stirred for 2 days. After addition of saturated $NaHCO_3$, the mixture was extracted three times with $CH_2Cl_2$. The organic extracts were combined and evaporated to dryness, and the product was purified by silica chromatography (90:9:1 toluene/acetone/$Et_3N$) to give 477 mg of product; LC-MS shows $[M+H]^+=$ 850.6.

B. 2'-O-Benzoyl-6-O-methyl-4", 11-bis(O-methanesulfonyl)-14,15-dehydroerythromycin A A solution of 2'-O-benzoyl-6-O-methyl-14,15-dehydroerythromycin A (549 mg) and methanesulfonyl chloride (0.50 mL) in 2.39 mL of pyridine was stirred for 24 hours, then diluted with $CH_2Cl_2$ and saturated $NaHCO_3$. The mixture was extracted three times with $CH_2Cl_2$. The organic extracts were combined and evaporated to dryness, and the product was purified by silica chromatography (90:9:1 toluene/acetone/$Et_3N$) to give 530 mg of product; LC-MS shows $[M+H]^+=1006.5$.

C. 2'-O-Benzoyl-6-O-methyl-4"-O-methanesulfonyl-10,11-anhydro-14,15-dehydroerythromycin A A mixture of 2'-O-benzoyl-6-O-methyl-4",10, 11-bis(O-methanesulfonyl)14,15-dehydroerythromycin A (59 mg) and diazabicycloundecene (0.018 mL) in 0.195 mL of acetone was stirred for 24 hours, then dried in vacuo. The product was purified by silica chromatography (90:9:1 toluene/acetone/$Et_3N$) to give 50 mg of product; LC-MS shows $[M+H]^+=910.5$.

D. 2'-O-Benzoyl-6-methyl-3-descladinosyl-10,11-anhydro-14,15-dehydroerythromycin A A mixture of 2'-O-benzoyl-6-O-methyl-4"-O-methanesulfonyl-10,11-anhydro-14,15-dehydroerythromycin A (337 mg), 1.5 mL of acetonitrile, and 6.9 mL of 3 N HCl was stirred for 22 hours. The acetonitrile was removed in vacuo, the pH of the aqueous residue was adjusted to 12 by addition of NaOH, and the product was extracted using 4 portions of $CH_2Cl_2$. The combined extracts were dried and evaporated. The product was purified by silica chromatography (gradient from 96:4 $CH_2Cl_2$/MeOH to 95:4:1 $CH_2Cl_2$/MeOH/$Et_3N$) to give 197 mg, $[M+H]^+=674.4$.

E. 2'-O-Benzoyl-6-O-methyl-3-descladinosyl-3-oxo-10,11-anhydro-14,15-dehydroerythromycin A A suspension of 2'-O-benzoyl-6-O-methyl-3-descladinosyl-10,11-anhydro-14,15-dehydroerythromycin A (226 mg) and the Dess-Martin periodinane (427 mg) in 14.6 mL of $CH_2Cl_2$ (14.6 ml.) was stirred for 1 hour. The mixture was diluted with $CH_2Cl_2$ and saturated $NaHCO_3$. The product was extracted using 3 portions of $CH_2Cl_2$, and the extracts were combined, dried, and evaporated. Silica gel chromatography (90:9:1 toluene/acetone/$Et_3N$) yielded the product, 168 mg. $[M+H]^-=672.4$.

$^{13}$C-NMR ($CDCl_3$, 100 MHz): δ206.78, 203 (br), 168.19, 165.08, 141.36, 139.58, 132.74, 131.51, 130.46, 129.79, 128.25, 120.18, 102.09, 80.79, 80.40, 78.70, 72.52, 71.91, 69.19, 63.76, 51.10, 50.54, 47.08, 40.73, 39.87, 37.77, 31.23, 22.13, 20.98, 18.52, 14.28, 14.15, 13.55.

Example 9

Synthesis of 5-O-(2'-acetyldesosaminyl)-10,11-anhydro-3-deoxy-3-oxo-6-O-methyl-15-methylerythron (Anhydro form of Formula (1); $R_a=$ OH, $R_d=$propyl, $R_f=$Me, $R_b=$H, $R_c=$Ac)

A. 6-O-methyl-3-descladinosyl-15-methylerythromycin A

A mixture of 6-O-methyl-15-methylerythromycin A (15.1 g) and 280 mL of 0.5 N HCl was stirred at ambient temperature for 3 hours. The pH was adjusted to 9 by addition of 6 N NaOH, and the resulting precipitate was collected by vacuum filtration, washed with water, and dried. The filtrate was extracted three times with 400-mL portions of ethyl acetate. The organic extracts were combined, washed sequentially with saturated $NaHCO_3$, water, and brine, then dried over $MgSO_4$, filtered, and evaporated to provide further product. The combined crude products were chromatographed on silica gel to yield 9.35 g of pure 6-O-methyl-3-descladinosyl-15-methylerythromycin A. ES-LC/MS shows $[M+H]^-=605$.

B. 2'-O-Acetyl-6-O-methyl-3-descladinosyl-15-methylerythromycin A

A solution of acetic anhydride (2.92 mL) in 35 mL of ethyl acetate was added dropwise to a solution of 6-O-methyl-3-descladinosyl-15-methylerythromycin A (9.35 g) in 40 mL of ethyl acetate. The mixture was stirred for 30 minutes after completion of addition, then concentrated. Chromatography on silica gel (2:1 hexanes/acetone) gave 8.35 g of 2'-O-acetyl-6-O-methyl-3-descladinosyl-15-methylerythromycin A. ES-LC/MS shows $[M+H]^-=647$.

C. 2'-O-Acetyl-6-O-methyl-3-descladinosyl-3-oxo-15-methylerythromycin A

A solution of 2'-O-acetyl-6-O-methyl-3-descladinosyl-15-methylerythromycin A (8.3 g) and 1-ethyl-3-(dimethylaminopropyl)carbodiimide hydrochloride (16.51 g) in 64 mL of dichloromethane and 15.47 mL of methyl-sulfoxide was placed under inert atmosphere and cooled on ice. A solution of pyridinium trifluoroacetate (16.63 g) in 64 mL of dichloromethane was added at a rate such that addition would be complete in 4 hours, and the reaction was monitored by thin-layer chromatography. Complete reaction was observed after addition of 73% of the solution, and so the reaction was then quenched by addition of 600 mL of ethyl acetate and 200 mL of saturated $NaHCO_3$. The organic layer was collected and washed sequentially with saturated $NaHCO_3$, water, and brine, then dried over $MgSO_4$, filtered, and evaporated to yield 8.4 g of crude product. Chromatography on silica gel (3:1 hexanes/acetone) gave 6.75 g of 2'-O-acetyl-6-O-methyl-3-descladinosyl-3-oxo-15-methylerythromycin A. ES-LC/MS shows $[M+H]^-=645$.

D. 2'-O-Acetyl-6-O-methyl-3-descladinosyl-3-oxo-11O-methanesulfonyl-15-methylerythromycin A Methanesulfonylchloride (5.68 mL) was added dropwise to a solution of 2'-O-acetyl-6-O-methyl-3-descladinosyl-3-oxo-15-methylerythromycin A (6.73 g) in 35 mL of pyridine at 0° C. The mixture was brought to ambient temperature and quenched by addition of 700 mL of ethyl acetate and 200 mL of saturated $NaHCO_3$. The organic layer was collected and washed sequentially with saturated $NaHCO_3$, water, and brine, then dried over $MgSO_4$, filtered, and evaporated to yield 8.2 g of crude product. Chromatography on silica gel (5:2 hexanes/acetone) gave 5.04 g of 2'-O-acetyl-6-O-methyl-3-descladinosyl-3-oxo-11-O-methanesulfonyl-15-methylerythromycin A. ES-LC/MS shows $[M+H]^-=723$.

E. 2'-O-Acetyl-6-O-methyl-3-descladinosyl-3-oxo-10,11-anhydro-15-methylerythromycin A 1,8-Diazabicyclo[5.4.0]undec-7-ene (5.22 mL) was added dropwise to a solution of 2'-O-acetyl-6-O-methyl-3-descladinosyl-3-oxo-11-methanesulfonyl-15-methylerythromycin A (5.03 g) in 23 mL of acetone. The solution was concentrated after 4.5 hours, and the residue was chromatographed on silica gel (5:2 hexanes/acetone) to give 3.72 g of 2'-O-acetyl-6-O-methyl-3-descladinosyl-3- oxo-10,11-anhydro-15-methylerythromycin A. ES-LC/MS shows [M+H]$^+$=627.

Example 10

Synthesis of 5-O-(2'-acetyldesosaminyl)-10,11-anhydro-3,6-dideoxy-3-oxo-15-methylerythronolide A (Formula (1), anhydro form, $R_a$=OH, $R_d$=propyl, $OR_f$ replaced by H, $R_b$=H, $R_c$=Ac)

To a solution of 6-deoxy-15-methyl erythromycin C (220 mg, 0.307 mmol) in dichloromethane (5 mL) were given potassium carbonate (50 mg) and acetic anhydride (100 L, 0.9 mmol), and the reaction was stirred at room temperature for 16 hours. The solution was filtered, sodium hydroxide (1N, 25 mL) and brine (25 mL) added and the aqueous layer was extracted with ethyl acetate 6 times. The combined organic layers were dried with sodium sulfate, filtered, and the solvent removed in vacuo. The crude product the 2' acetylated form of the starting material was carried on to the next step.

The crude product was dissolved in pyridine (5 mL) and mesyl chloride (70 L, 0.9 mmol) was added. The reaction was stirred at −20° C. for 2 days, poured on sodium hydroxide (1N, 25 mL) and brine (25 mL) and the aqueous layer was extracted with ethyl acetate 6 times. The combined organic layers were dried with sodium sulfate, filtered, and the solvent removed in vacuo. The residue was purified by chromatography on silica gel (toluene/acetone=3:1, 1% ammonium hydroxide) to yield 11,4"-dimesylated form (190 mg, 68% over two steps).

The 11, 4"-dimesylated form (190 mg, 0.21 mmol) was dissolved in acetone (7 mL) and DBU (63 L, 0.42 mmol) was added, and the reaction was stirred at room temperature over night. The mixture was poured on sodium hydroxide (1 N, 25 mL) and brine (25 mL) and the aqueous layer was extracted with ethyl acetate 6 times. The combined organic layers were dried with sodium sulfate, filtered, and the solvent removed in vacuo. The crude product, the 10,11-dehydro form of 6-deoxy-15-methyl erythromycin was carried on to the next step.

To the crude product from the above step was added hydrochloric acid (30 mL, 3 N) and ethanol (2 mL) and the mixture was stirred vigorously for 6 hours. Sodium hydroxide (5 mL, 10 N) was added and the aqueous layer was extracted with ethyl acetate 6 times. The combined organic layers were dried with sodium sulfate, filtered, and the solvent removed in vacuo. The crude product, the anhydro form of formula (1) (but with OH at position 3) where $R_a$=OH, $R_d$=propyl, $OR_f$ is replaced by H, $R_b$=$R_c$=H, was carried on to the next step.

To the crude product from the above step in dichloromethane (5 mL) was added acetic anhydride (50 L, 0.45 mmol) and potassium carbonate (100 mg) and the mixture was stirred vigorously for 9 hours. The reaction was filtered, sodium hydroxide (20 mL, 1N) and brine (25 mL) were added and the aqueous layer was extracted with ethyl acetate 6 times. The combined organic layers were dried with sodium sulfate, filtered, and the solvent removed in vacuo. The residue was purified by chromatography on silica gel (toluene/acetone=3:1, 1% ammonium hydroxide) to yield the 2' acetylated form of the starting material (110 mg, 89% over three steps).

The product of the above step (110 mg, 0.184 mmol) was dissolved in dichloromethane (10 mL) and Dess-Martin reagent (220 mg, 0.53 mmol) was added. The reaction was stirred at room temperature for 45 min. The reaction was quenched with Sodium hydroxide (20 mL, 1 N) and brine (25 mL) and the aqueous layer was extracted with ethyl acetate 6 times. The combined organic layers were dried with sodium sulfate, filtered, and the solvent removed in vacuo. The residue was purified by chromatography on silica gel (toluene/acetone, gradient=6:1–3:1, 1% ammonium hydroxide) to yield the compound of formula (1), anhydro form, where $R_a$=OH, $R_d$=propyl, $OR_f$ is replaced by H, $R_b$=H, $R_c$=OAc (94 mg, 86%).

Example 11

I. Compound of Formula (3):$R_a$=OH, $R_d$=propyl, $R_f$=allyl

Step 1. Allylation of Intermediate Antibiotic at 6-OH A solution of 2',4"-bis-O-trimethylsilyl-15-methylerythromycin A 9-[O-(1-isopropoxycyclohexyl)] oxime (formula (I) ($R_a$, is OH, $R_d$ is propyl, protected at 2' and 4" with trimethylsilyl and at C9=O by the isoproxy-cyclohexyl oxime)) (7.8 g, 7.44 mmol) in 30 mL of tetrahydrofuran was cooled on ice and treated with 30 mL of methylsulfoxide and 2.58 mL of freshly distilled allyl bromide under inert atmosphere. A mixture of methylsulfoxide (29.8 mL) and 1.0 M potassium tert-butoxide in tetrahydrofuran (29.8 mL) was added at a rate of 1.33 molar equivalents of base per hour. The reaction was monitored by thin-layer chromatography (silica gel, 10:1 toluene/acetone), and was judged complete after addition of 3.6 molar equivalents of base. The reaction was diluted with 700 mL of ethyl acetate and washed sequentially with saturated NaHCO$_3$, water, and brine. The organic phase was dried with MgSO$_4$, filtered, and evaporated to yield 8.08 g of crude 6-O-allyl-2',4"-bis-O-trimethylsilyl-15-methylerythromycin A 9-[O-(1-isopropoxycyclohexyl)]oxime. This was carried on without further purification.

Step 2:

A solution of 6-O-allyl-2',4"-bis-O-trimethylsilyl-15-methylerythromycin A 9-[O-(1-isopropoxycyclohexyl)] oxime (8.08 g) in 42 mL of acetonitrile was treated with 21 mL of water and 24 mL of acetic acid, and stirred for 18 hours at ambient temperature. The mixture was concentrated after addition of 2-propanol, then repeatedly after addition of toluene to yield 7.7 g of crude product. Chromatography on silica gel (gradient from 2:1 to 1:1 hexanes/acetone +1% Et$_3$N) gave 3.75 g of 6-O-allyl-15-methylerythromycin A 9-oxime.

Step 3

A solution of 6-O-allyl-15-methylerythromycin A 9-oxime (3.75 g) and sodium hydrosulfite (85%, 5.37 g) in 66 mL of 1:1 ethanol/water was placed under inert atmosphere. Formic acid (0.845 mL) was added dropwise, and the mixture was stirred at 80° C. for 3.5 hours. After cooling to ambient temperature, the reaction was adjusted to pH 10 with 6 N NaOH and extracted three times with 150-mL portions of ethyl acetate. The organic extracts were combined and washed sequentially with saturated NaHCO$_3$, water, and brine. The organic phase was dried with MgSO$_4$, filtered, and evaporated to yield 3.42 g of 6-O-allyl-15-methylerythromycin A suitable for further conversion.

II. Compound of Formula (3): $R_a$=OH, $R_d$=Me, $R_f$=allyl

Step 1: Allylation of Intermediate Antibiotic at 6—OH

A solution of 2',4"-bis-O-trimethylsilyl-14-norerythromycin A 9-[O-(1-isopropoxycyclohexyl)]oxime, Formula (I), ($R_a$ is OH, $R_d$ is methyl, protected at 2' and 4" with trimethylsilyl and at C9=O by the isoproxycyclohexyl oxime) (202 mg) in tetrahydrofuran (0.4 mL), DMSO (0.4 mL), and ether (0.04 mL) was cooled to 10° C. and treated with 0.035 mL of freshly distilled allyl bromide under inert atmosphere. A mixture of methylsulfoxide (0.4 mL) and 1.0 M potassium tert-butoxide in tetrahydrofuran (0.4 mL) was added at a rate 0.22 mL/hour. The reaction was monitored by thin-layer chromatography (silica gel, 5:1 toluene/acetone). The reaction was diluted with ethyl acetate and washed sequentially with saturated $NaHCO_3$, water, and brine. The organic phase was dried with $MgSO_4$, filtered, and evaporated to yield 222 mg of crude 6-O-allyl-2',4"-bis-O-trimethylsilyl-14-norerythromycin A 9-[O-(1-isopropoxycyclohexyl)]oxime. This was carried on without further purification.

Step 2

A solution of 6-O-allyl-2',4"-bis-O-trimethylsilyl-14-norerythromycin A 9-[O-(1-isopropoxycyclohexyl)]oxime (222 mg) in 4 mL of acetonitrile was treated with 2 mL of water and 2.4 mL of acetic acid, and stirred for 18 hours at ambient temperature. The mixture was concentrated after addition of 2-propanol, then repeatedly after addition of toluene to yield 220 mg of crude 6-O-allyl-14-norerythromycin A 9-oxime.

Step 3

A solution of 6-O-allyl-14-norerythromycin A 9-oxime (220 mg) and sodium hydrosulfite (85%, 322 mg) in 4 mL of 1:1 ethanol/water was placed under inert atmosphere. Formic acid (0.050 mL) was added dropwise, and the mixture was stirred at 80° C. for 15 hours. After cooling to ambient temperature, the reaction was adjusted to pH 10 with 6 N NaOH and extracted three times with 150-mL portions of ethyl acetate. The organic extracts were combined and washed sequentially with saturated $NaHCO_3$, water, and brine. The organic phase was dried with $MgSO_4$, filtered, and evaporated to yield 156 mg of 6-O-allyl-14-norerythromycin A suitable for further conversion.

Other Embodiments

In a similar manner, compounds of formula (3) wherein Y and Z are, together, =O, $R_a$ is OH, $R_f$ is allyl, is prepared from an intermediate where $R_d$ is butyl, benzyl, vinyl, or 3-hydroxybutyl.

Example 12

Conversion to Formula (1)

Step 1

A mixture of the compound prepared in Example 11, II (77 mg, crude), 0.073 ml of 12 N HCl and water (2 ml) was stirred at ambient temperature for 3 hours. The mixture was brought to pH 8 with 8 N KOH, and extracted with ethyl acetate. The organic extract was washed with brine, dried with $MgSO_4$, filtered, and evaporated. The residue was chromatographed on silica gel (3:1/hexanes:acetone, 1% triethylamine) to give pure product as a white solid (42 mg).

Step 2

To protect the 2' OH, a mixture the above compound (73 mg), potassium carbonate(20 mg), acetic anhydride (14 µl) and acetone (1 ml) was stirred at ambient temperature for 18 hours. Ethyl acetate was added, washed with water and brine, dried over $MgSO_4$, filtered, and evaporated. The residue was chromatographed on silica gel (3:1/hexanes:acetone, 1% triethylamine) to yield the pure product (71 mg) as a white solid.

Step 3

A solution of the compound resulting from step 2 (99 mg) and 1-(3-dimethylaminopropyl)-3-ethylcarbodiidmide (EDC) hydrochloride (206 mg) in dichloromethane (2 ml) was treated with DMSO (0.21 ml) and cooled to 5° C. A solution of pyridinium trifluoroacetate (208 mg) in dichloromethane (2 ml) was added via a syringe pump in 4 hours. Ethyl acetate was then added, washed with saturated $NaHCO_3$, water, brine, and dried over $MgSO_4$, filtered, and evaporated. The residue was chromatographed on silica gel (3:1/hexanes:acetone, 1% triethylamine) to yield the pure compound of formula (1) (94 mg, $R_a$ is OH, $R_c$ is acetate, $R_d$ is $CH_3$, and $R_f$ is allyl).

Step 4

To deprotect 2' OH, a solution of the compound resulting from step 3 (94 mg) in 5 mL methanol was stirred at room temperature for 24 hours. The solvent was removed in vacuo to give the desired compound of formula (1) ($R_a$ is OH, $R_c$ is H, $R_d$ is $CH_3$, and $R_f$ is allyl).

Other Embodiments

In a similar manner, compounds of formula (1) wherein $R_a$ is OH, $R_c$ is H, $R_f$ is allyl, and $R_d$ is propyl, butyl, benzyl, vinyl, or 3-hydroxybutyl is prepared.

Example 13

Preparation of Compounds of Formula (2)

The compound of formula (3), prepared as the 6-allyl derivative in Example 11, is protected at the 2' position, treated with acid and dehydrated, then deprotected to obtain the compound of formula (2), as shown in FIG. 1, wherein $R_a$ is OH, $R_c$ is H, and $R_f$ is allyl. Similarly, compounds of formula (1) wherein $R_d$ is propyl, butyl, benzyl, vinyl, or 3-hydroxybutyl, are prepared as described above using as starting material the compounds of formula (1) wherein $R_d$ is as set forth above.

Example 14

Conversion of =O at Position 9 to =NOH

According to the procedure of Example 6A, the carbonyl at position 9 of erythromycins are converted to the corresponding oximes.

Example 15

Conversions at —$OR_f$

A. Allyl→Propyl

A solution of any of the compounds prepared above (0.2 mmol) in ethanol is flushed with nitrogen and 10% palladium on carbon (20 mg) added. The mixture is then flushed with hydrogen and the reaction mixture stirred overnight under positive hydrogen pressure. The reaction mixture is filtered and concentrated in vacuo to give a glass. Chromatography on silica gel (95:5:0.5 dichloromethane-methanol-ammonia) gives the propyl compounds as white solids.

B. Allyl→—$CH_2CHO$

Ozone is passed through a −78° C. solution in dichloromethane (100 mL) of any of the compounds resulting above (4.0 mmol) for 45 minutes. The reaction mixture is then flushed with nitrogen for 10 minutes. Dimethyl sulfide (1.46 mL, 20 mmol) is added at −78° C. and the reaction mixture stirred for 30 minutes at 0° C. The reaction mixture is concentrated in vacuo to give a white foam which is used without further purification by heating a solution of the compound in THF (40 mL, 4.0 mmol) and triphenylphosphine (2.62 g, 10.0 mmol) at 55° C. for 2.5 hours. The reaction mixture is concentrated in vacuo to give a white foam. Chromatography on silica gel (1:1 acetone-hexane, then 75:25:0.5 acetone-hexane-triethylamine) gives the desired compound as a white solid.

C. Allyl→—$CH_2CH$=NOH

To a solution in methanol (5 mL) of the compound prepared in B wherein $R_f$ is —$CH_2CHO$, (0.08 mmol) is added triethylamine (31 μL, 0.225 mmol) and hydroxylamine hydrochloride (7.7 mg, 0.112 mmol) and the reaction mixture stirred for 6 hours at ambient temperature. The reaction mixture is taken up in ethyl acetate and washed with aqueous 5% sodium bicarbonate and brine, dried over sodium sulfate, and concentrated in vacuo to give a clear glass. Chromatography on silica gel (95:5:0.5 dichloromethane-methanol-ammonia) gives the compound as a white solid.

D. —$CH_2CH=NOH \rightarrow$ —$CH_2CN$

To a solution under nitrogen of the compound prepared in C (0.267 mmol) in THF (5 mL) is added diisopropylcarbodiimide (83 μL, 0.534 mmol) and CuCl (2.7 mg, 0.027 mmol) and the reaction mixture is stirred overnight at ambient temperature. The reaction mixture is taken up in ethyl acetate and washed with aqueous 5% sodium bicarbonate and brine, dried over sodium sulfate, and concentrated in vacuo to give a clear glass. Chromatography on silica gel (95:5:0.5 dichloromethane-methanol-ammonia) gives the desired compound as a white solid.

E. —$CH_2CHO \rightarrow$ —$CH_2CH_2NH_2$

To a solution in methanol (10 mL) of the compound prepared in B (0.276 mmol) is added ammonium acetate (212 mg, 2.76 mmol) and the mixture is cooled to 0° C. Sodium cyanoborohydride (34 mg, 0.553 mmol) is added and the reaction mixture stirred for 30 hours at 0° C. The reaction mixture is taken up in ethyl acetate and washed with aqueous 5% sodium carbonate, aqueous 2% tris(hydroxymethyl)aminomethane, and brine, dried over sodium sulfate, filtered, and concentrated in vacuo. Chromatography on silica gel (90:10:0.5 dichloromethane-methanol-ammonia) gives the desired compound as a white solid.

F. —$CH_2CHO \rightarrow$ —$CH_2CH_2NHCH_2$-Phenyl

To a 0° C. solution in methanol (10 mL) of the compound prepared in B (0.200 mmol) is added acetic acid (114 μL, 2.00 mmol) and benzylamine (218 μL, 2.00 mmol) and the mixture is stirred for 10 minutes. Sodium cyanoborohydride (24.8 mg, 0.400 mmol) is added and the reaction mixture stirred for 16 hours. Additional sodium cyanoborohydride (24.8 mg, 0.400 mmol) is then added and stirring continued for 5 hours. The reaction mixture is taken up in ethyl acetate and washed with aqueous 5% sodium carbonate, aqueous 2% tris(hydroxymethyl)aminomethane, and brine, dried over sodium sulfate, filtered, and concentrated in vacuo. Chromatography on silica gel (95:5:0.5 dichloromethane-methanol-ammonia) followed by a second chromatography (50:50:0.5 acetone-hexanes-triethylamine) gives the desired compound as a white foam.

G. —$CH_2CHO \rightarrow$ —$CH_2CH_2NHCH_2CH_2$-Phenyl

To a 0° C. solution in methanol (10 mL) of the compound prepared in B (0.200 mmol) is added acetic acid (114 μL, 2.00 mmol) and phenethylamine (218 μL, 2.00 mmol) and the mixture is stirred for 10 minutes. Sodium cyanoborohydride (24.8 mg, 0.400 mmol) is added and the reaction mixture stirred for 16 hours. The reaction mixture is taken up in ethyl acetate and washed with aqueous 5% sodium carbonate, aqueous 2% tris(hydroxymethyl)aminomethane, and brine, dried over sodium sulfate, filtered, and concentrated in vacuo. Chromatography on silica gel (90:10:0.5 dichloromethane-methanol-ammonia) gives the desired compound.

H. —$CH_2CHO \rightarrow$ —$CH_2CH_2NHCH(CO_2CH_3)CH_2$-Phenyl

To a 0° C. solution in methanol (10 mL) of the compound prepared in B (0.200 mmol) is added L-phenylalanine methyl ester hydrochloride (129 mg, 0.600 mmol) and the mixture stirred for 10 minutes. Sodium cyanoborohydride 924.8 mg, 0.400 mmol) is added and the reaction mixture stirred for 22 hours. The reaction mixture is taken up in ethyl acetate and washed with aqueous 5% sodium carbonate, aqueous 2% tris(hydroxymethyl)aminomethane, and brine, dried over sodium sulfate, filtered, and concentrated in vacuo. Chromatography on silica gel (95:5:0.5 dichloromethane-methanol-ammonia) gives the desired compound.

I. —$CH_2CHO \rightarrow$ —$CH_2CH_2NHCH_2$-(4-pyridyl)

The desired compound is prepared according to the method in G, except substituting 4-aminomethylpyridine for phenethylamine.

J. —$CH_2CH_2NH_2 \rightarrow$ —$CH_2CH_2NHCH_2$-(4-quinolyl)

To a solution of the compound prepared in E (0.15 mmol) in methanol (2 mL) is added 4-quinolinecarboxaldehyde (23 mg, 0.15 mmol), acetic acid (8.6 μL, 0.15 mmol), and sodium cyanoborohydride (9.4 mg, 0.15 mmol) and the reaction mixture is stirred for 15 hours. The reaction mixture is taken up in ethyl acetate and washed with aqueous 5% sodium carbonate, aqueous 2% tris(hydroxymethyl) aminomethane, and brine, dried over sodium sulfate, filtered, and concentrated in vacuo. Chromatography on silica gel (95:10:0.5 dichloromethane-methanol-ammonia) gives the desired compound.

K. Allyl$\rightarrow$—$CH_2CH=CH$-Phenyl

To a solution under nitrogen of the 2' protected compound prepared in Example 10 (1.00 mmol), palladium(II)acetate (22 mg, 0.100 mmol), and triphenylphosphine (52 mg, 0.200 mmol) in acetonitrile (5 mL) was added iodobenzene (220 μL, 2.00 mmol) and triethylamine (280 μL, 2.00 mmol) and the mixture is cooled to −78° C., degassed, and sealed. The reaction mixture is then warmed to 60° C. for 0.5 hours and stirred at 80° C. for 12 hours, taken up in ethyl acetate and washed twice with aqueous 5% sodium bicarbonate, once with aqueous 2% tris(hydroxymethyl)aminomethane, and once with brine, dried over sodium sulfate, filtered, and concentrated in vacuo. Chromatography on silica gel (95:5:0.5 dichloromethane-methanol-ammonia) gives the desired compound.

Deprotection is accomplished by heating in methanol.

Other embodiments of formulas (1)–(3) where $R_b$ is H, $R_c$ is H, $R_a$ is OH, Y and Z are together =O and $R_d$ is propyl, butyl, benzyl, vinyl, or 3-hydroxybutyl are those wherein $R_f$ is:

—$CH_2CH_2CH_2$-phenyl;
—$CH_2CH=CH$-(4-methoxyphenyl);
—$CH_2CH=CH$-(4-chlorophenyl);
—$CH_2CH=CH$-(3-quinolyl);
—$CH_2CH_2CH_2OH$;
—$CH_2C(O)OH$;
—$CH_2CH_2NHCH_3$;
—$CH_2CH_2NHCH_2OH$;
—$CH_2CH_2N(CH_3)_2$;
—$CH_2CH_2$(1-morpholinyl);
—$CH_2C(O)NH_2$;
—$CH_2NHC(O)NH_2$;
—$CH_2NHC(O)CH_3$;
—$CH_2F$;
—$CH_2CH_2OCH_3$;
—$CH_2CH_3$;
—$CH_2CH=CH(CH_3)_2$;
—$CH_2CH_2CH(CH_3)CH_3$;
—$CH_2CH_2OCH_2CH_2OCH_3$;

—$CH_2SCH_3$;
—cyclopropyl;
—$CH_2OCH_3$;
—$CH_2CH_2F$;
—$CH_2$-cyclopropyl;
—$CH_2CH_2CHO$;
—$C(O)CH_2CH_2CH_3$;
—$CH_2$-(4-nitrophenyl);
—$CH_2$-(4-chlorophenyl);
—$CH_2$-(4-methoxyphenyl);
—$CH_2$-(4-cyanophenyl);
—$CH_2CH=CHC(O)OCH_3$;
—$CH_2CH=CHC(O)OCH_2CH_3$;
—$CH_2CH=CHCH_3$;
—$CH_2CH=CHCH_2CH_3$;
—$CH_2CH=CHCH_2CH_2CH_3$;
—$CH_2CH=CHSO_2$-phenyl;
—$CH_2C\equiv CSi(CH_3)_3$
—$CH_2C\equiv CCH_2CH_2CH_2CH_2CH_2CH_3$;
—$CH_2C\equiv CCH_3$;
—$CH_2$-(2-pyridyl);
—$CH_2$-(3-pyridyl);
—$CH_2$-(4-pyridyl);
—$CH_2$-(4-quinolyl);
—$CH_2NO_2$;
—$CH_2C(O)OCH_3$;
—$CH_2C(O)$-phenyl;
—$CH_2C(O)CH_2CH_3$;
—$CH_2Cl$;
—$CH_2S(O)_2$-phenyl;
—$CH_2CH=CHBr$;
—$CH_2CH=CH$-(4-quinolyl);
—$CH_2CH_2CH_2$-(4-quinolyl);
—$CH_2CH=CH$-(5-quinolyl);
—$CH_2CH_2CH_2$-(5-quinolyl);
—$CH_2CH=CH$-(4-benzoxazolyl); or
—$CH_2CH=CH$-(7-benzimidazolyl).

Any of the foregoing compounds can be converted to the corresponding derivatives wherein Y and Z are together=NOH in the manner described in Example 14 above.

Example 16

Fluorination of C2 Position

Synthesis of 2'-O-benzoyl-6-O-propargyl-3-descladinosyl-3-oxo-10,11-anhydro-2-fluoro-15-methylerythromycin A A solution of 2'-O-benzoyl -6-O-propargyl-3-descladinosyl-3-oxo-10,11-anhydro-15-methyl-erythromycin A in tetrahydrofuran under inert atmosphere is cooled to −78° C. and treated with 1.0 M potassium tert-butoxide in tetrahydrofuran. The mixture is stirred for 5 minutes, and a solution of N-fluorobenzenesulfonimide in tetrahydrofuran is added in three portions over 2 hours. After addition, the reaction is allowed to warm to ambient temperature and kept for an additional 5 hours. Aqueous $K_2CO_3$ is added, and the mixture is extracted with $CH_2Cl_2$. The organic extracts are combined, dried over $MgSO_4$, filtered, and evaporated. Chromatography on silica gel gives the product.

Example 17

Derivatization of C-13 Position

Starting Material: 15-Aminoerythromycin A diacetate salt

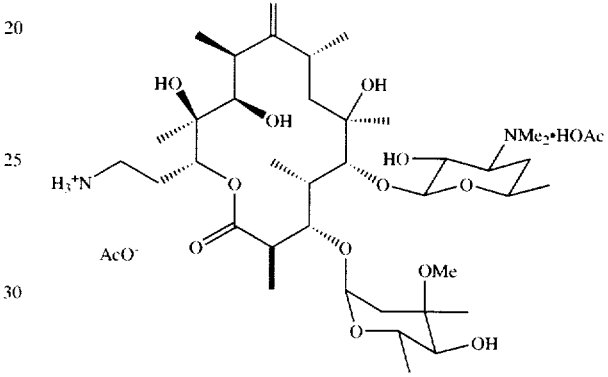

A solution of 15-azidoerythromycin A (7.75 g, 10 mmol) in 50 mL of methanol is treated with acetic acid (2.0 mL) and 10% palladium on carbon (0.1 g) and stirred under 1 atm of hydrogen gas until thin-layer chromatographic analysis reveals complete reduction of the starting material. The suspension is filtered through Celite to remove the catalyst, then evaporated to dryness to yield the product, which is used as a starting material for the following derivatizations.

A. Synthesis of 15-(quinol-4-ylacetamido) erythromycin A

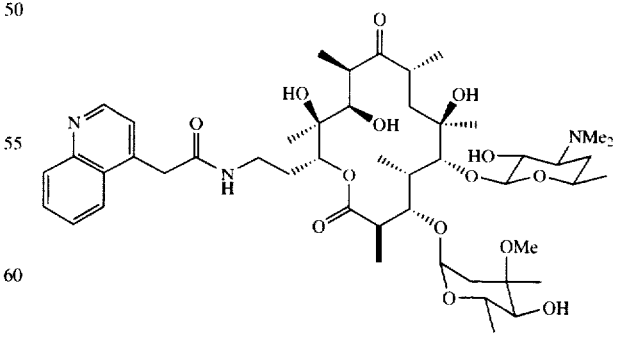

A solution of 15-Aminoerythromycin A diacetate salt (1.0 g) in 10 mL of dichloromethane is treated sequentially with quinol-4-ylacetyl chloride (350 mg) and triethylamine (0.5 mL) at 0° C. After 3 hours, the reaction is diluted with dichloromethane and washed three times with saturated aqueous NaHCO₃. The organic phase is dried over MgSO₄, filtered, and evaporated to yield the crude product. Purification by silica gel chromatography yields the pure product.

B. Synthesis of 15-(3-(quinol-4-yl)propionamido) erythromycin A

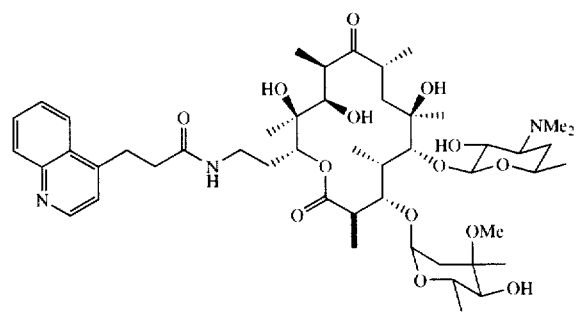

A solution of 15-aminoetythromycin A diacetate salt (1.0 g) in 10 mL of dichloromethane is treated sequentially with 3-(quinol-4-yl)propionyl chloride (400 mg) and triethylamine (0.5 mL) at 0° C. After 3 hours, the reaction is diluted with dichloromethane and washed three times with saturated aqueous NaHCO₃. The organic phase is dried over MgSO₄, filtered, and evaporated to yield the crude product. Purification by silica gel chromatography yields the pure product.

C. Synthesis of 15-(isoquinol-4-ylacetamido) erythromycin A

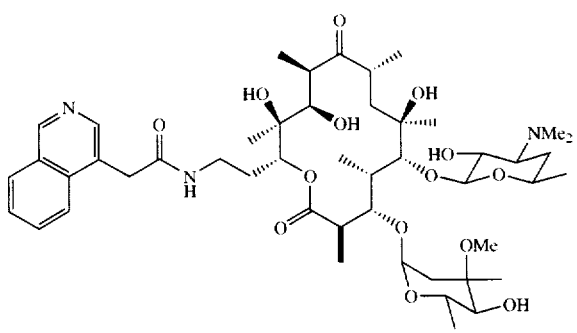

A solution of 15-aminoerythromycin A diacetate salt (1.0 g) in 10 mL of dichloromethane is treated sequentially with isoquinol-4-ylacetyl chloride (350 mg) and triethylamine (0.5 mL) at 0° C. After 3 hours, the reaction is diluted with dichloromethane and washed three times with saturated aqueous NaHCO₃. The organic phase is dried over MgSO₄, filtered, and evaporated to yield the crude product. Purification by silica gel chromatography yields the pure product.

D. Synthesis of 15-(3-(isoquinol-4-yl) propionamido)erythromycin A

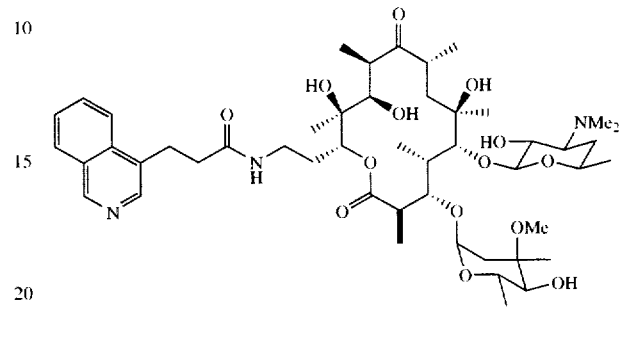

A solution of 15-aminoerythromycin A diacetate salt (1.0 g) in 10 mL of dichloromethane is treated sequentially with 3-(isoquinol-4-yl)propionyl chloride (400 mg) and triethylamine (0.5 mL) at 0° C. After 3 hours, the reaction is diluted with dichloromethane and washed three times with saturated aqueous NaHCO₃. The organic phase is dried over MgSO₄, filtered, and evaporated to yield the crude product. Purification by silica gel chromatography yields the pure product.

E. Synthesis of 15-((quinol-5-ylamino)acetamido) erythromycin A

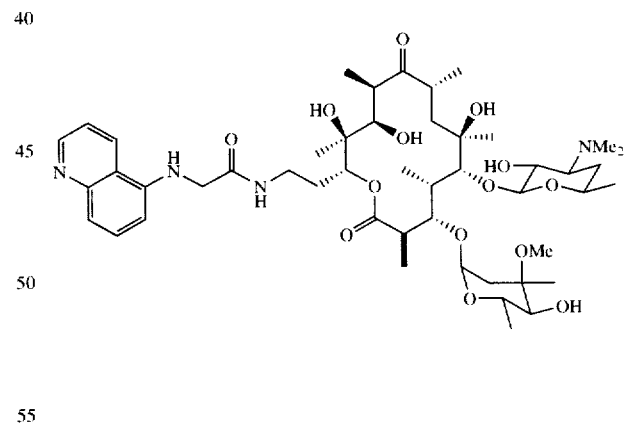

A solution of 15-aminoerythromycin A diacetate salt (1.0 g) in 10 mL of dichloromethane is treated sequentially with (quinol-5-ylamino)acetic acid (0.30 g), dicyclohexylcarbodiimide (0.4 g), 1-hydroxybenzotriazole (0.25 g), and triethylamine (0.5 mL) at 0° C. After 3 hours, the reaction is diluted with dichloromethane and washed three times with saturated aqueous NaHCO₃. The organic phase is dried over MgSO₄, filtered, and evaporated to yield the crude product. Purification by silica gel chromatography yields the pure product.

F. Synthesis of 15-((quinol-6-ylamino)acetamido)erythromycin A

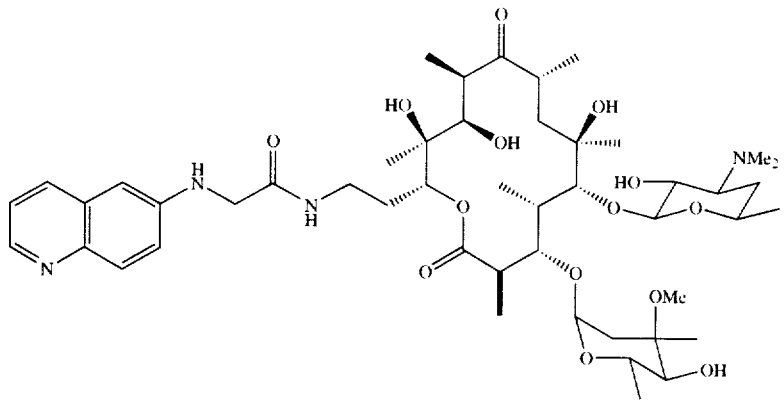

A solution of 15-aminoerythromycin A diacetate salt (1.0 g) in 10 mL of dichloromethane is treated sequentially with (quinol-6-ylamino)acetic acid (0.30 g), dicyclohexylcarbodiimide (0.4 g), 1-hydroxybenzotriazole (0.25 g), and triethylamine (0.5 mL) at 0° C. After 3 hours, the reaction is diluted with dichloromethane and washed three times with saturated aqueous NaHCO$_3$. The organic phase is dried over MgSO$_4$, filtered, and evaporated to yield the crude product. Purification by silica gel chromatography yields the pure product.

G. Synthesis of 15-((quinol-4-ylmethyl)carbamoylamino)erythromycin A

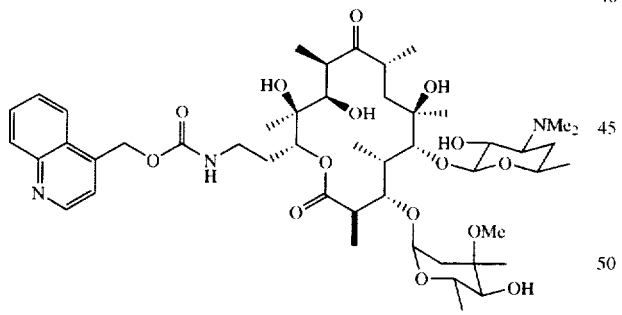

A solution of 15-aminoerythromycin A diacetate salt (1.0 g) in 10 mL of dichloromethane is treated sequentially with quinoline-4-methoxycarbonyl chloride (400 mg) and triethylamine (0.5 mL) at 0° C. After 3 hours, the reaction is diluted with dichloromethane and washed three times with saturated aqueous NaHCO$_3$. The organic phase is dried over MgSO$_4$, filtered, and evaporated to yield the crude product. Purification by silica gel chromatography yields the pure product.

What is claimed is:

1. A compound of the formula

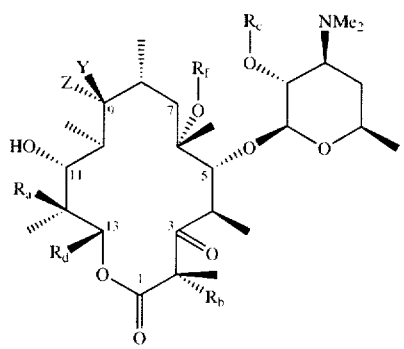

(1)

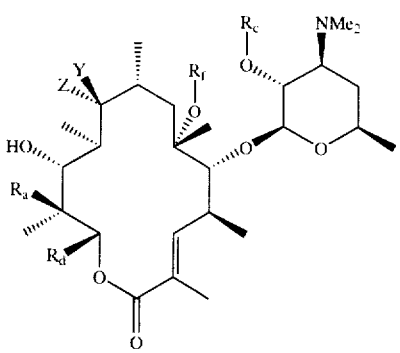

(2)

45

-continued
or

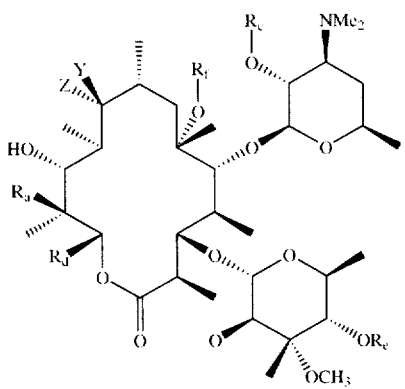

(3)

or a pharmaceutically acceptable salt thereof or a stereoisomeric form thereof or a mixture of stereoisomeric forms thereof wherein:

$R_a$ is H or OH;
$R_b$ is H or halogen;
$R_c$ is H or a protecting group;
$R_d$ is substituted or unsubstituted amidoarylalkyl (5–20° C.); substituted or unsubstituted amidoarylalkenyl (5–20° C.); or substituted or unsubstituted amidoarylalkynyl (5–20° C.);
$R_e$ is H or a protecting group or is mono- or disubstituted amino carbonyl;
$R_f$ is H, C1–C3 alkyl, allyl or propargyl; and, one of Z and Y is H and the other is OH or protected OH, or is amino, mono- or dialkyl-amino, protected amino, or an aminoheterocycle or
Z and Y together are =O, =NOH, or =NOR where R is C1–C12 alkyl.

2. The compound of claim 1 wherein $R_c$ and $R_e$ are each H; and Z and Y together are =O.
3. The compound of claim 2 wherein $R_a$ is OH; and $R_b$ is H or F.
4. The compound of claim 3 wherein $R_f$ is H.
5. The compound of claim 3 wherein $R_f$ is allyl.
6. The compound of claim 3 wherein $R_f$ is propargyl.
7. The compound of claim 3 wherein $R_f$ is methyl and $R_b$ is H.
8. The compound of claim 3 wherein Rf is methyl and Rb is H.
9. A pharmaceutical composition comprising an effective amount of the compound of claim 1 in admixture with a pharmaceutically acceptable excipient.
10. A method to control infection in a subject which method comprises administering to a subject in need of such

46 control an effective amount of the compound of claim 1 or a pharmaceutical composition thereof.

11. A method to preserve material from microbial decay which method comprises providing said material with an effective amount of the compound of claim 1.
12. A compound of the formula

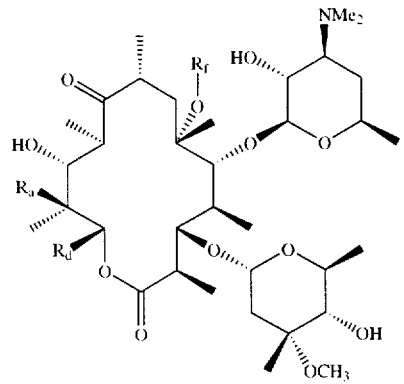

wherein:

$R_a$ is H or OH;
$R_d$ is substituted or unsubstituted amidoarylalkyl (5–20° C.); substituted or unsubstituted amidoarylalkenyl (5–20° C.); or substituted or unsubstituted amidoarylalkynyl (5–20° C.); and,
$R_f$ is H, C1–C3 alkyl, allyl or propargyl.
13. The compound of claim 12 wherein $R_a$ is OH;
$R_d$ is substituted or unsubstituted amidoarylalkyl (5–20° C.); and,
$R_f$ is H.
14. The compound of claim 12 wherein $R_a$ is OH;
$R_d$ is substituted or unsubstituted amidoarylalkyl (5–20° C.); and,
$R_f$ is methyl.
15. The compound of claim 12 wherein $R_a$ is OH;
$R_d$ is substituted or unsubstituted amidoarylalkyl (5–20° C.); and,
$R_f$ is allyl.
16. The compound of claim 12 wherein $R_a$ is OH;
$R_d$ is substituted or unsubstituted amidoarylalkyl (5–20° C.); and,
$R_f$ is propargyl.
17. The compound of claim 12 of the formula

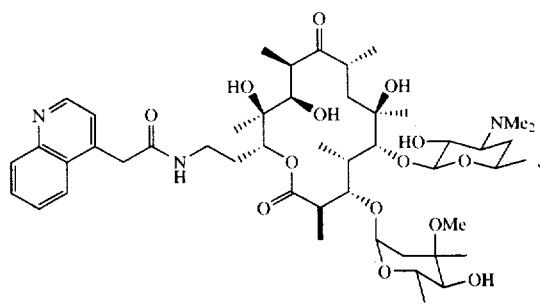

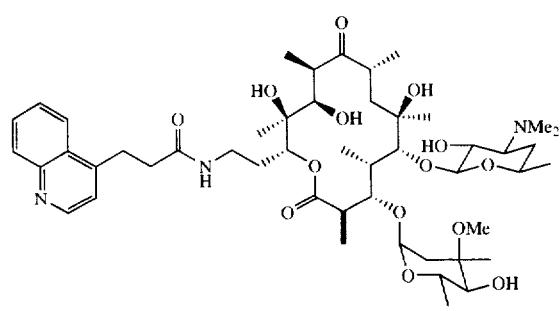

-continued
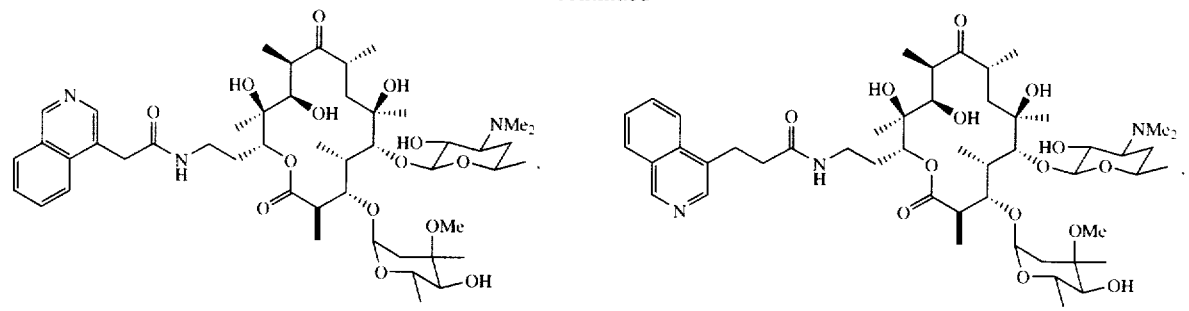
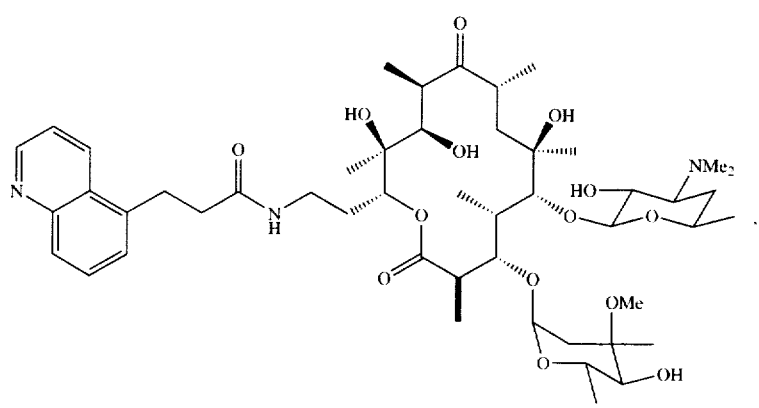
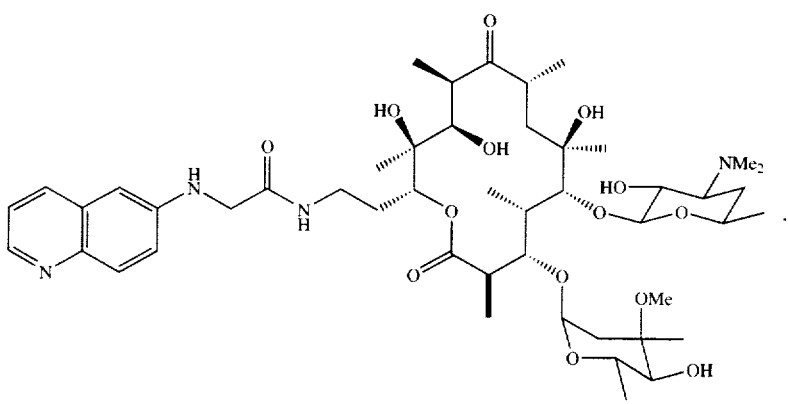
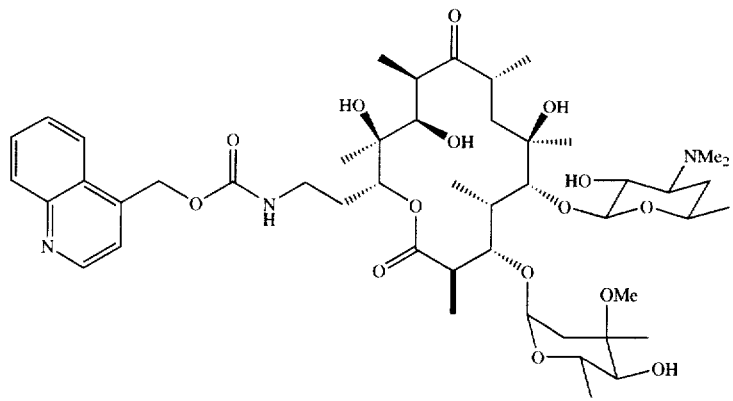

18. A compound of the formula

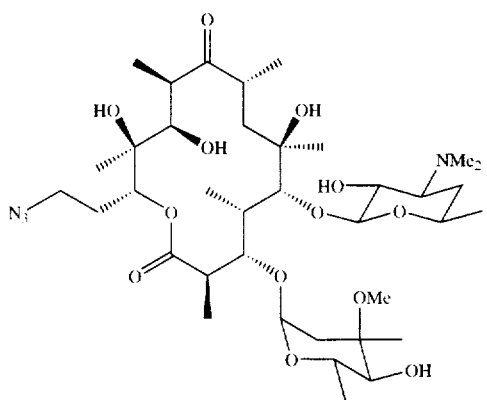

19. A compound of the formula

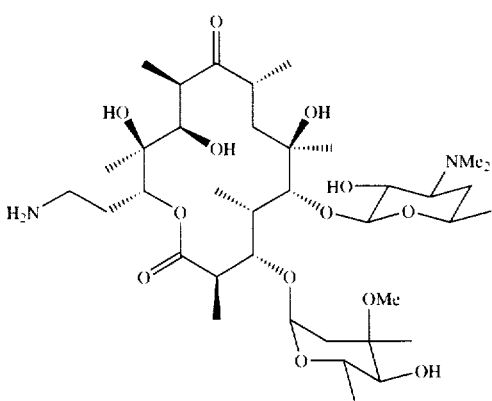

20. A compound of the formula

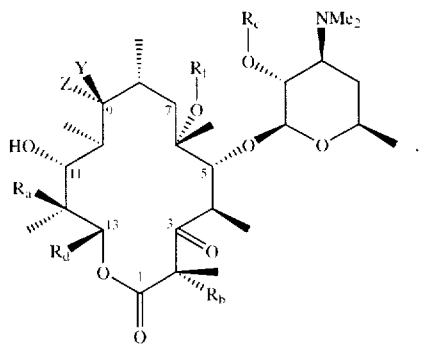

(1)

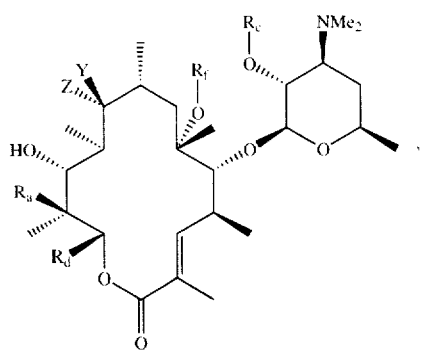

(2)

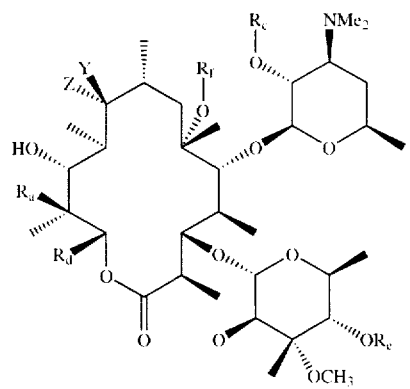

(3)

or pharmaceutically acceptable salt thereof or a stereoisomeric form thereof or a mixture of stereoisomeric forms thereof wherein:

$R_a$ is H or OH;

$R_b$ is H or halogen;

$R_c$ is H or a protecting group;

$R_d$ is C1–C10 alkyl substituted with —$N_3$, —NRR' or —NRCOR' wherein R and R' are each independently H; substituted or unsubstituted alkyl; substituted or unsubstituted alkenyl; substituted or unsubstituted alkynyl; substituted or unsubstituted aryl; or substituted or unsubstituted arylalkyl;

$R_e$ is H or a protecting group or is mono- or disubstituted amino carbonyl;

$R_f$ is H, C1–C3 alkyl, allyl or propargyl; and, one of Z and Y is H and the other is OH or protected OH, or is amino, mono- or dialkyl-amino, protected amino, or an aminoheterocycle or Z and Y together are =O, =NOH, or =NOR" where R" is C1–C12 alkyl.

21. The compound of claim 20 wherein $R_a$ is OH;

$R_b$ is H or F;

$R_c$ and $R_e$ are each H; and, $R_f$ is H, methyl, allyl or propargyl.

22. The compound of claim 20 of the formula

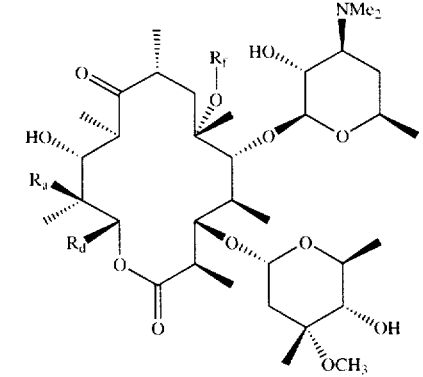

wherein:

$R_a$ is H or OH;

$R_d$ is C1–C10 alkyl substituted with —$N_3$, —NRR' or —NRCOR' wherein R and R' are each independently H; substituted or unsubstituted alkyl; substituted or unsubstituted alkenyl; substituted or unsubstituted alkynyl; substituted or unsubstituted aryl; or substituted or unsubstituted arylalkyl; and $R_f$ is H, C1–C3 alkyl, allyl or propargyl.

23. The compound as in claim 22 wherein $R_a$ is OH;

$R_d$ is C1–C10 alkyl substituted with —$N_3$; and $R_f$ is H.

24. The compound as in claim 22 wherein $R_a$ is OH;

$R_d$ is C1–C10 alkyl substituted with —NRR' wherein R and R' are each independently H; substituted or unsubstituted alkyl; substituted or unsubstituted aryl; or substituted or unsubstituted arylalkyl; and $R_f$ is H.

25. The compound as in claim 22 wherein $R_a$ is OH;

$R_d$ is C1–C10 alkyl substituted with —NRR' wherein R and R' are each independently H; and $R_f$ is H.

26. The compound of claim 22 wherein $R_a$ is OH;

$R_d$ is —$CH_2CH_2NRR'$ or —$CH_2CH_2NRCOR'$ wherein R and R' are each independently H; substituted or unsubstituted alkyl; substituted or unsubstituted alkenyl; substituted or unsubstituted alkynyl; substituted or unsubstituted aryl; or substituted or unsubstituted arylalkyl; and, $R_f$ is H.

27. The compound of claim 22 wherein $R_a$ is OH;

$R_d$ —$CH_2CH_2NRR'$ or —$CH_2CH_2NRCOR'$ wherein R and R' are each independently H; substituted or unsubstituted alkyl; substituted or unsubstituted alkenyl; substituted or unsubstituted alkynyl; substituted or unsubstituted aryl; or substituted or unsubstituted arylalkyl; and, $R_f$ is methyl.

* * * * *

UNITED STATES PATENT AND TRADEMARK OFFICE
Certificate

Patent No. 6,451,768 B1                                                               Patented: September 17, 2002

On petition requesting issuance of a certificate for correction of inventorship pursuant to 35 U.S.C. 256, it has been found that the above identified patent, through error and without any deceptive intent, improperly sets forth the inventorship.

Accordingly, it is hereby certified that the correct inventorship of this patent is: Daniel T. W. Chu, Santa Clara, CA; and Gary Ashley, Alameda, CA.

Signed and Sealed this Twenty-eighth Day of June 2005.

*JAMES O. WILSON*
*Supervisory Patent Examiner*
*Art Unit 1623*